(12) United States Patent
Kojima et al.

(10) Patent No.: US 12,274,467 B2
(45) Date of Patent: Apr. 15, 2025

(54) BALLOON CATHETER

(71) Applicant: KANEKA CORPORATION, Osaka (JP)

(72) Inventors: Masahiro Kojima, Settsu (JP); Takahisa Hamabuchi, Osaka (JP); Masato Tsueda, Settsu (JP)

(73) Assignee: KANEKA CORPORATION, Osaka (JP)

( * ) Notice: Subject to any disclaimer, the term of this patent is extended or adjusted under 35 U.S.C. 154(b) by 350 days.

(21) Appl. No.: 17/841,916

(22) Filed: Jun. 16, 2022

(65) Prior Publication Data

US 2022/0304718 A1 Sep. 29, 2022

Related U.S. Application Data

(63) Continuation of application No. PCT/JP2020/046382, filed on Dec. 11, 2020.

(30) Foreign Application Priority Data

Dec. 20, 2019 (JP) .................................. 2019-230874
Dec. 20, 2019 (JP) .................................. 2019-230875

(51) Int. Cl.
*A61B 17/3207* (2006.01)
*A61M 25/10* (2013.01)
*A61M 25/00* (2006.01)

(52) U.S. Cl.
CPC ... *A61B 17/320725* (2013.01); *A61M 25/104* (2013.01); *A61M 2025/0037* (2013.01)

(58) Field of Classification Search
CPC ........ A61B 17/320725; A61M 25/104; A61M 2025/0037; A61M 2025/1086; A61M 2025/109; A61M 2025/1093
See application file for complete search history.

(56) References Cited

U.S. PATENT DOCUMENTS 5,315,747 A 5/1994 Solar
5,413,557 A 6/1995 Solar
(Continued)

FOREIGN PATENT DOCUMENTS

JP 9-501852 A 2/1997
JP 2007-512873 A 5/2007
(Continued)

OTHER PUBLICATIONS

International Search Report, issued in PCT/JP2020/046382, dated Jan. 26, 2021.
(Continued)

*Primary Examiner* — Brooke Labranche
(74) *Attorney, Agent, or Firm* — Birch, Stewart, Kolasch & Birch, LLP

(57) ABSTRACT

Disclosed is a balloon catheter that can prevent or reduce axial rotation and circumferential shift of the elongate body while ensuring good passage of the balloon in the blood vessel. The balloon catheter (100) has a shaft (110); a balloon (120); an elongate body (180) extending along the shaft (110) and having a body tissue contacting part at its distal end part; and an elongate body lumen (130), the elongate body lumen (130) having a first engagement part (131) so that axial rotation angle of the elongate body (180) is 0° to 60°, and the first engagement part (131) being located between the distal end (130*d*) of the elongate body lumen (130) and a position 30 cm from the distal end of the elongate body lumen (130) toward the proximal side.

18 Claims, 15 Drawing Sheets

(56) References Cited

U.S. PATENT DOCUMENTS

| | | | |
|---|---|---|---|
| 5,531,690 | A | 7/1996 | Solar |
| 5,569,199 | A | 10/1996 | Solar |
| 5,669,880 | A | 9/1997 | Solar |
| RE36,104 | E | 2/1999 | Solar |
| 5,921,958 | A | 7/1999 | Ressemann et al. |
| 2005/0119678 | A1 | 6/2005 | O'Brien et al. |
| 2008/0200944 | A1 | 8/2008 | Hardert |
| 2010/0312264 | A1 | 12/2010 | O'Brien et al. |
| 2011/0288479 | A1* | 11/2011 | Burton ........... A61B 17/320725 604/103.08 |
| 2012/0130407 | A1 | 5/2012 | Aggerholm et al. |
| 2015/0150586 | A1 | 8/2015 | Aggerholm et al. |
| 2016/0058982 | A1 | 3/2016 | Aggerholm et al. |
| 2016/0128718 | A1 | 5/2016 | Aggerholm et al. |
| 2020/0305926 | A1 | 10/2020 | Tarunaga |

FOREIGN PATENT DOCUMENTS

| | | |
|---|---|---|
| JP | 2014-506140 A | 3/2014 |
| JP | 2015-104671 A | 6/2015 |
| JP | 2020-156734 A | 10/2020 |

OTHER PUBLICATIONS

Written Opinion of the International Searching Authority, issued in PCT/JP2020/046382, dated Jan. 26, 2021.

* cited by examiner

[FIG. 1]
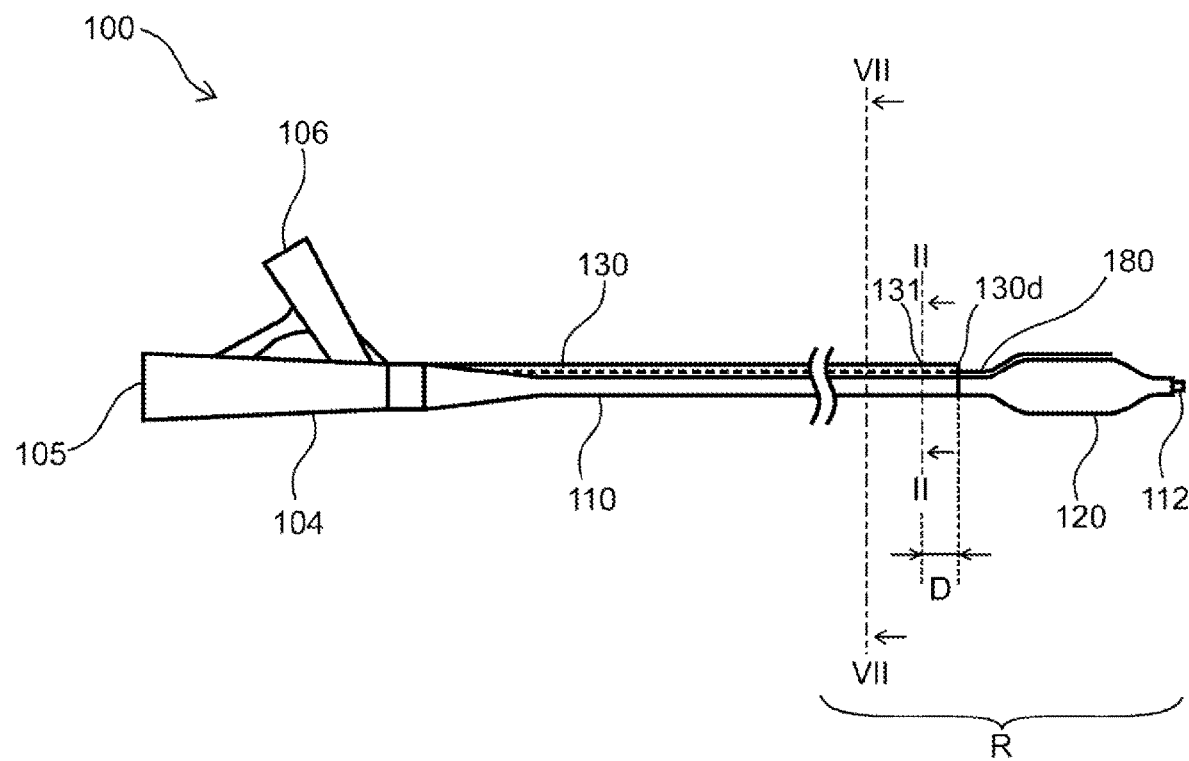
[FIG. 2]
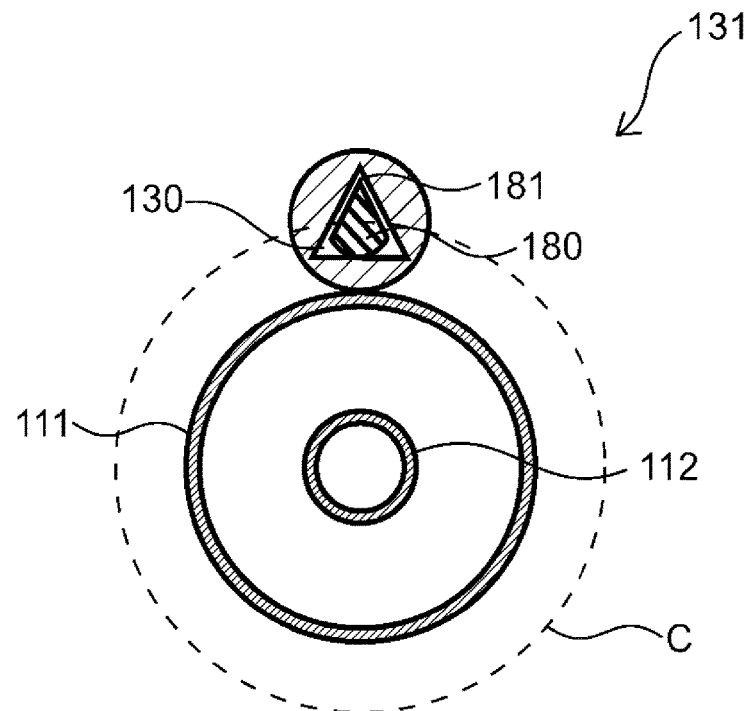

[FIG. 3]
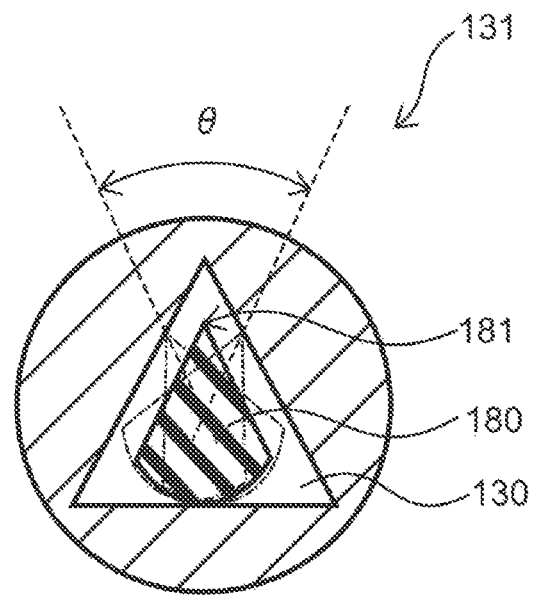
[FIG. 4]
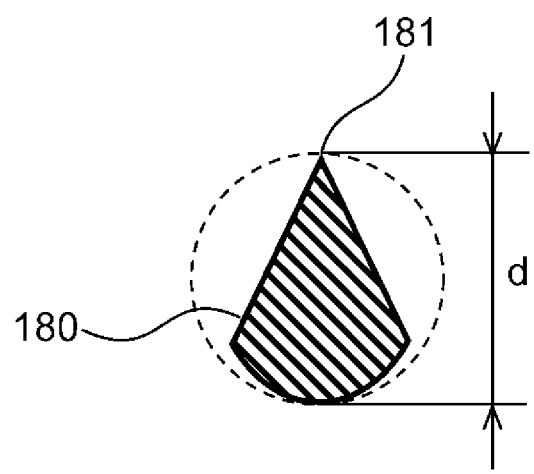

[FIG. 5]
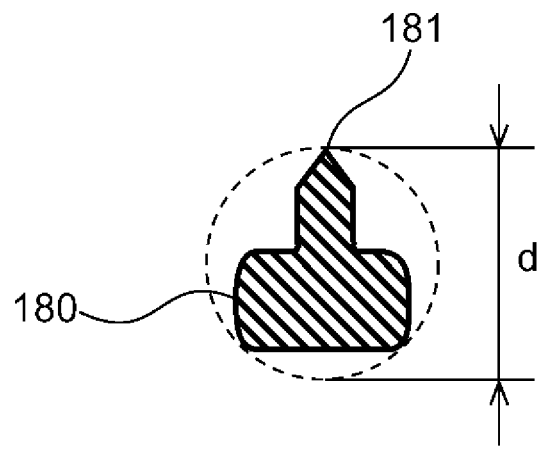
[FIG. 6]
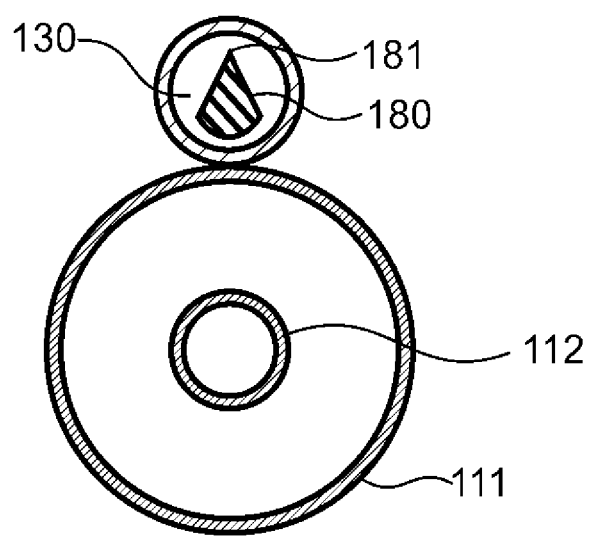

[FIG. 7]
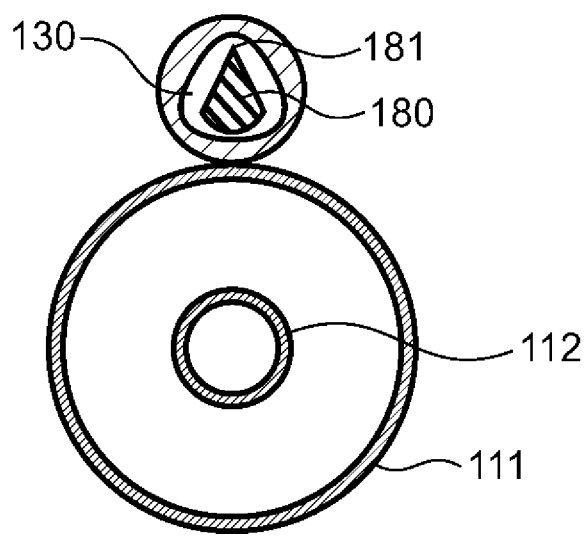
[FIG. 8]
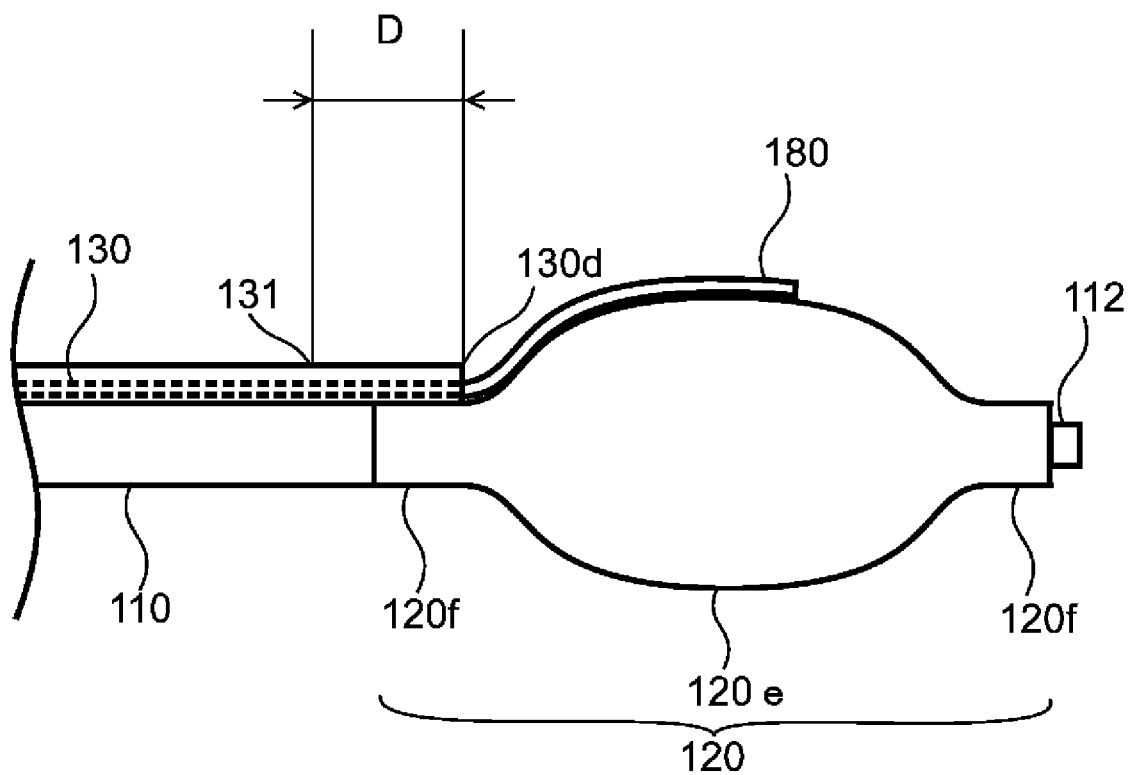

[FIG. 9]
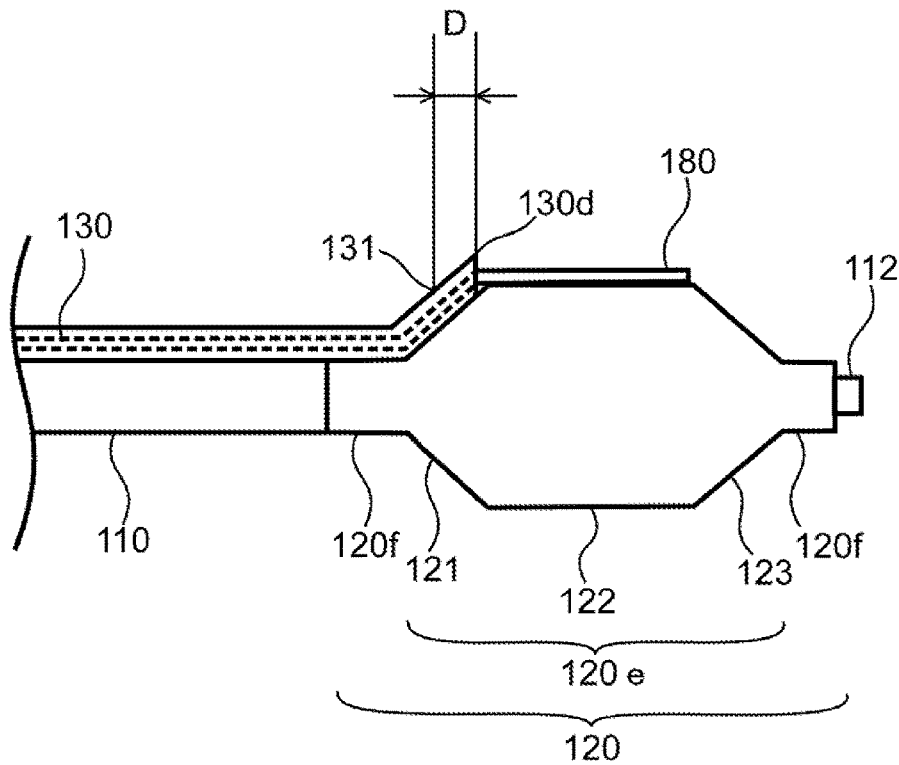
[FIG. 10]
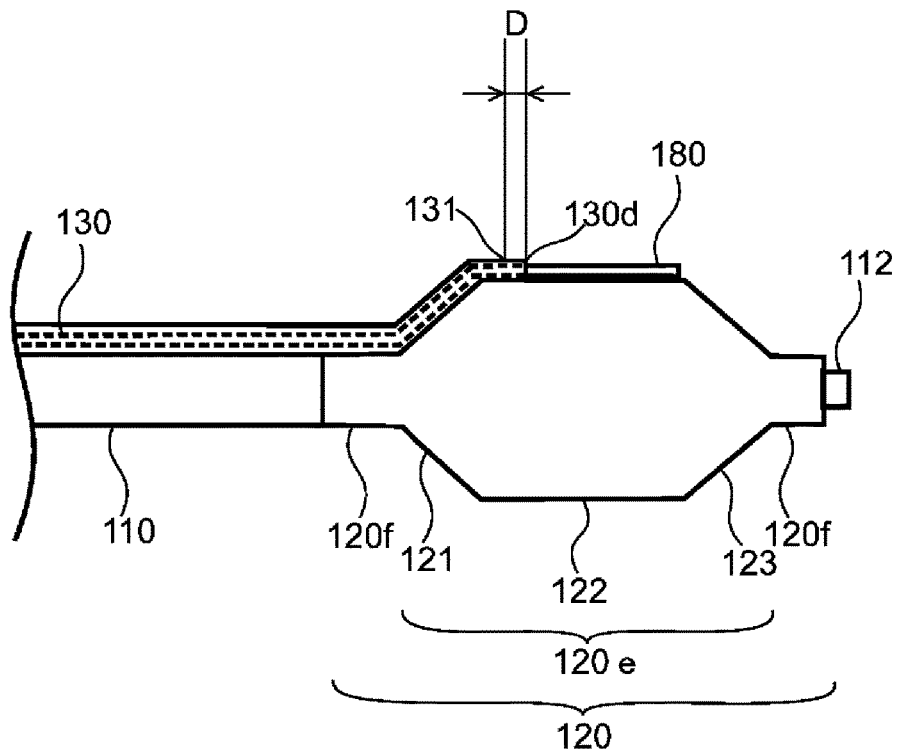

[FIG. 11]
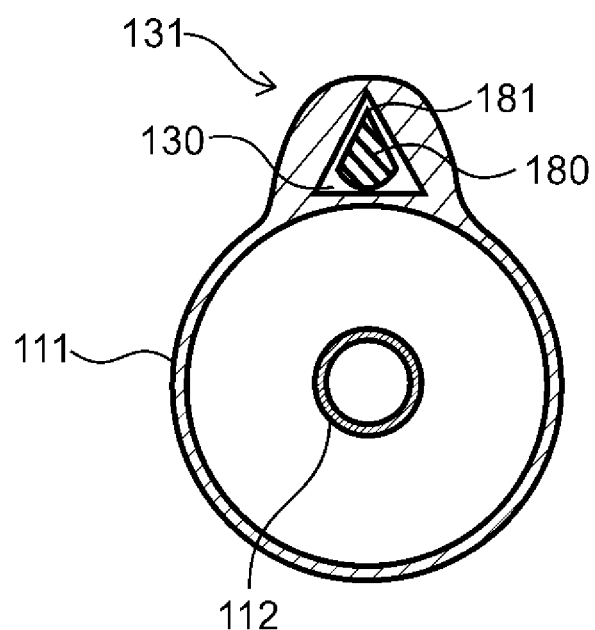
[FIG. 12]
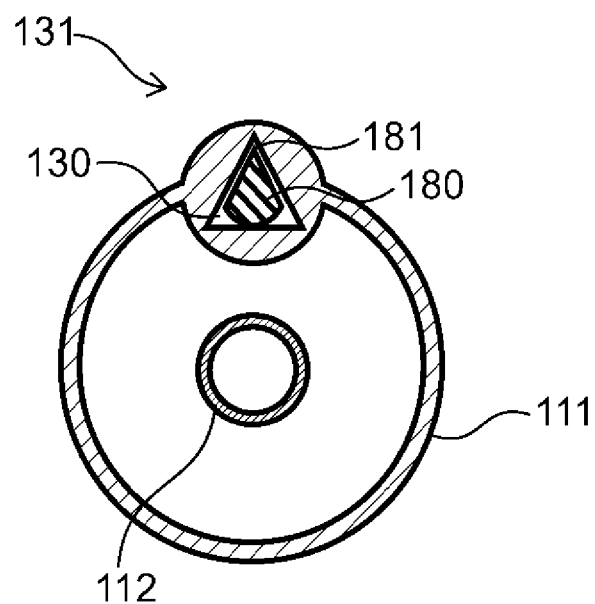

[FIG. 13]
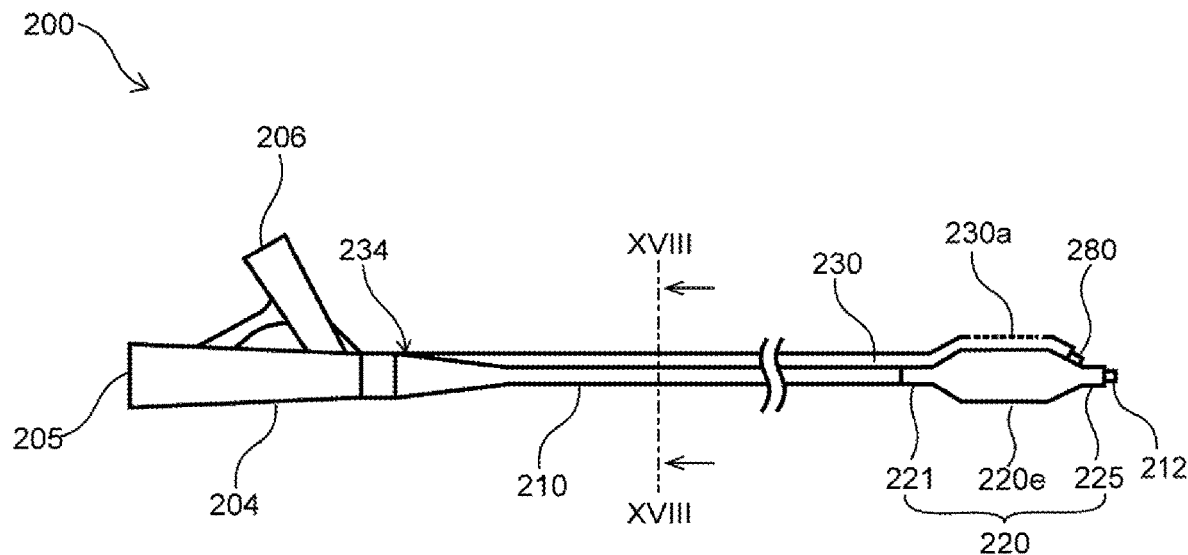
[FIG. 14]
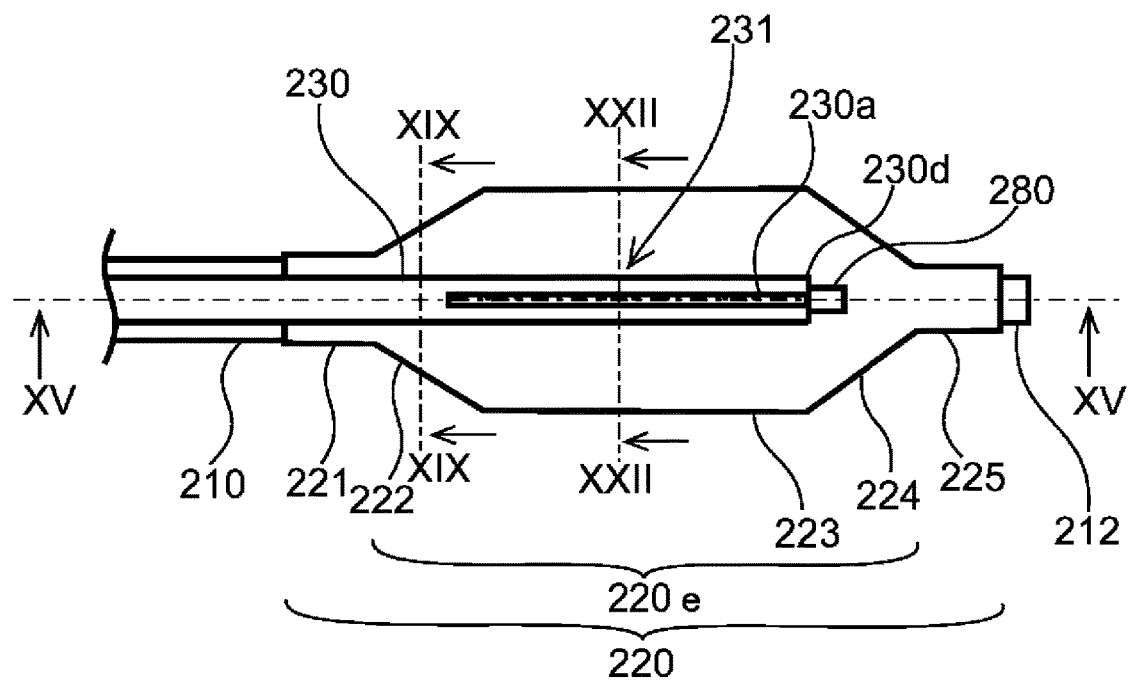

[FIG. 15]
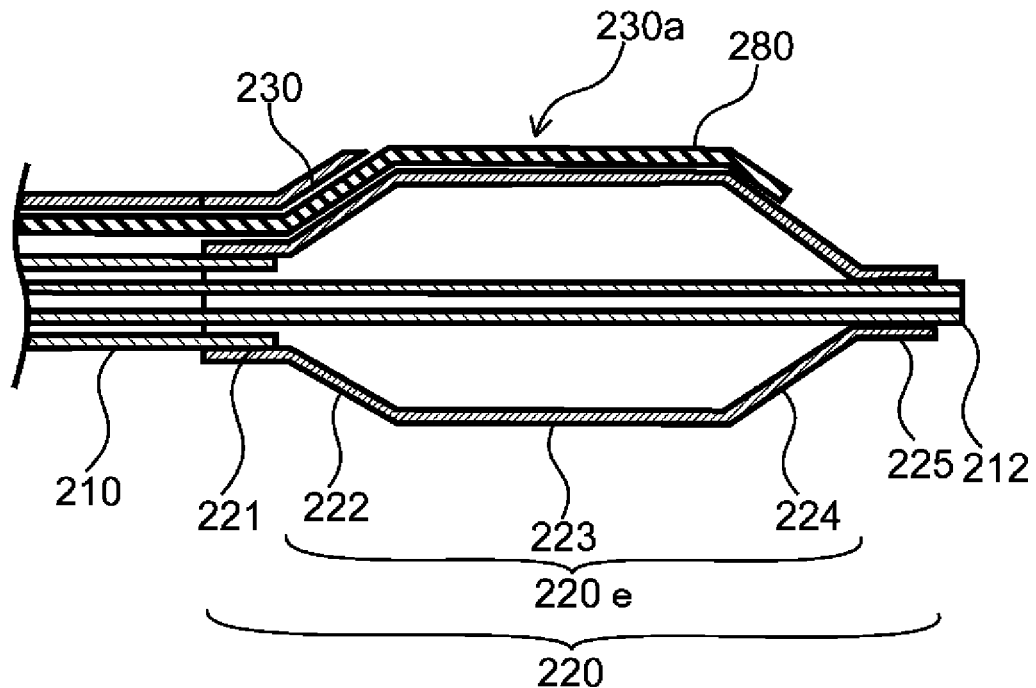
[FIG. 16]
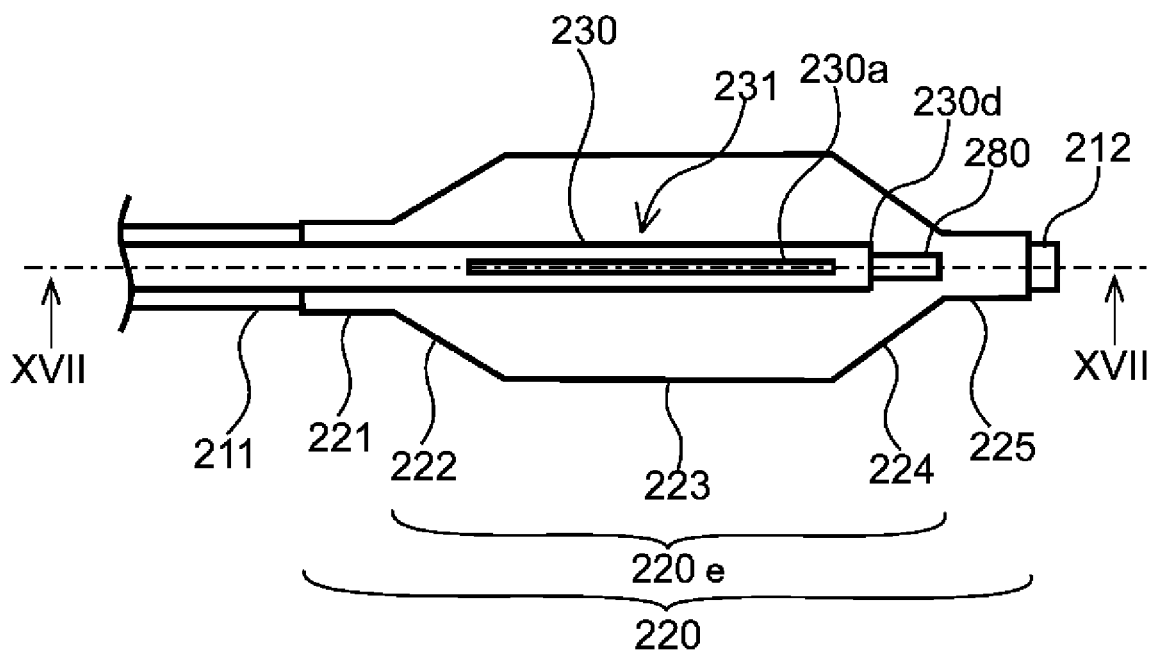

[FIG. 17]
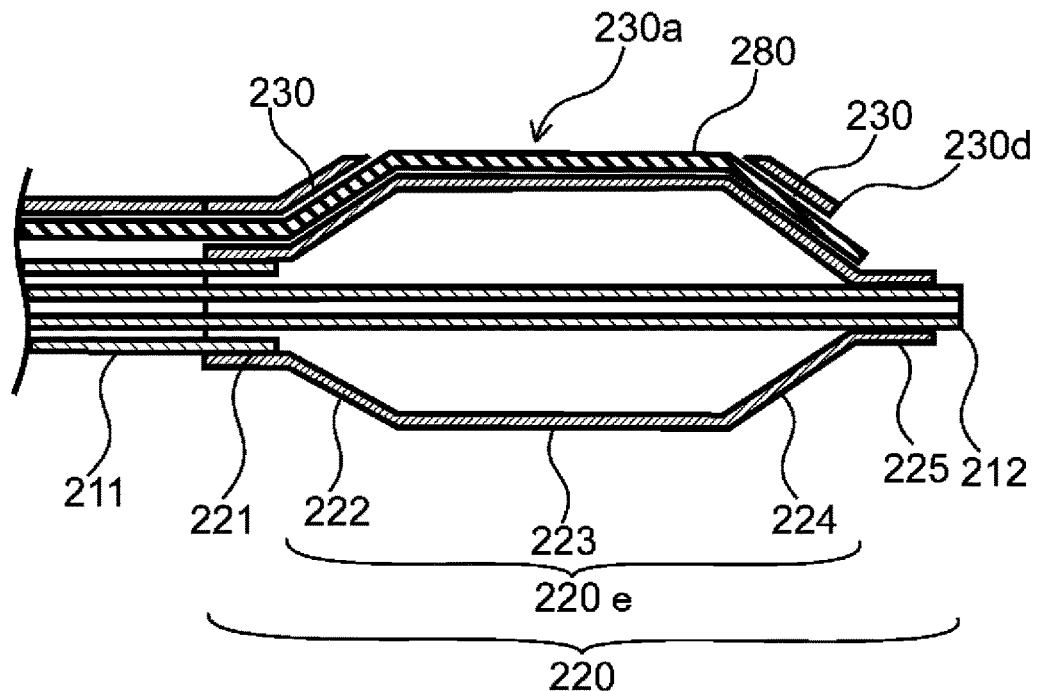
[FIG. 18]
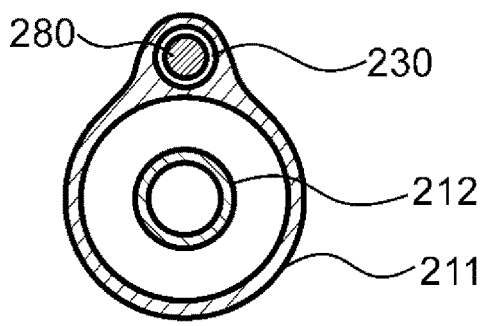
[FIG. 19]
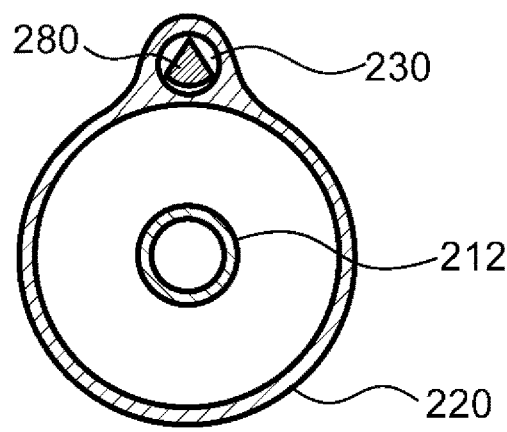

[FIG. 20]
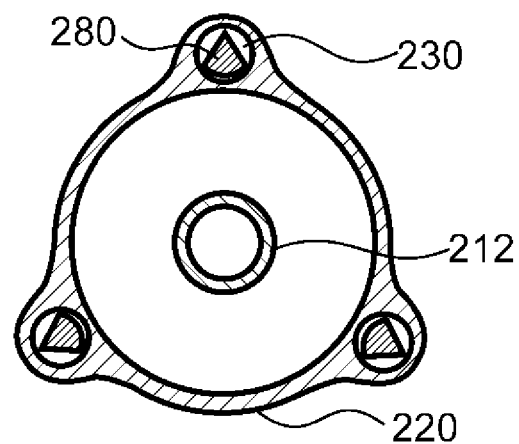
[FIG. 21]
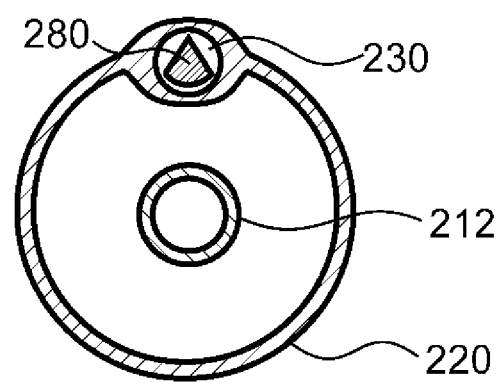
[FIG. 22]
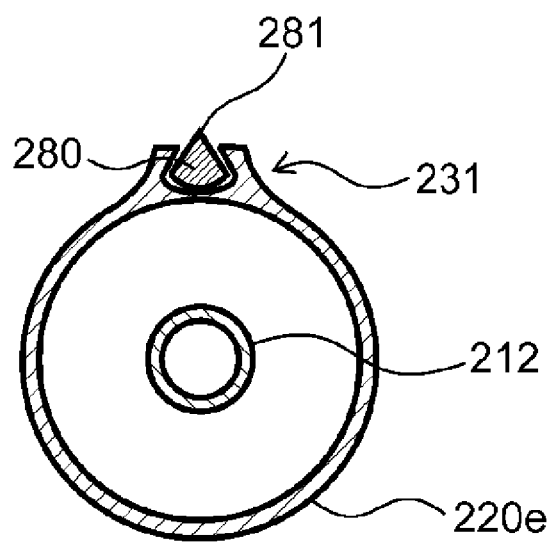

[FIG. 23]
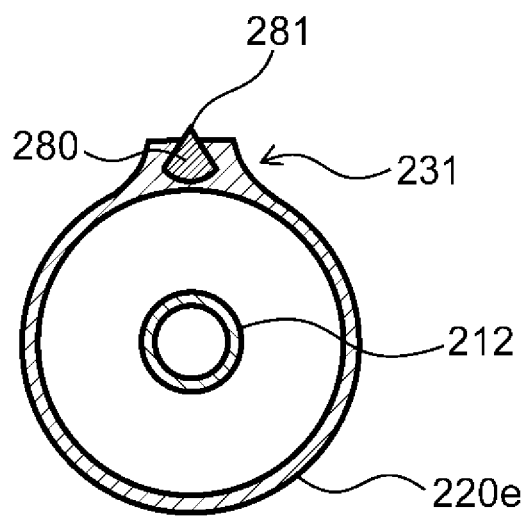
[FIG. 24]
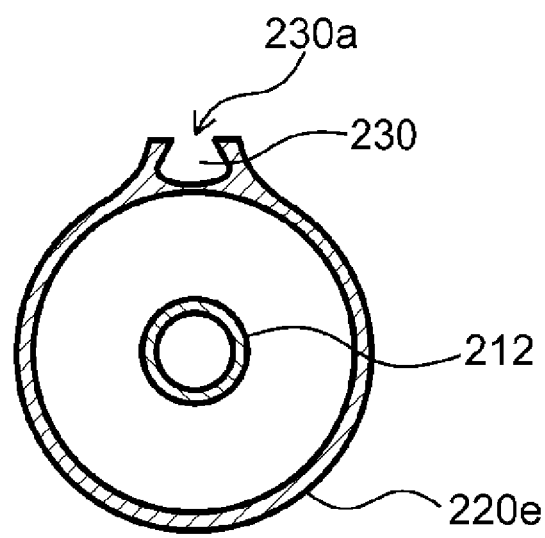
[FIG. 25]
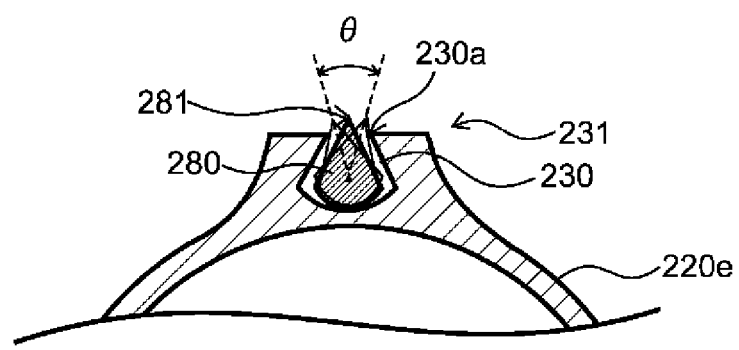

[FIG. 26]
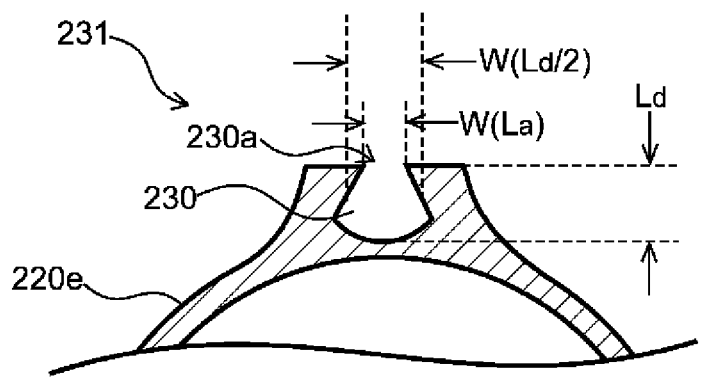
[FIG. 27]
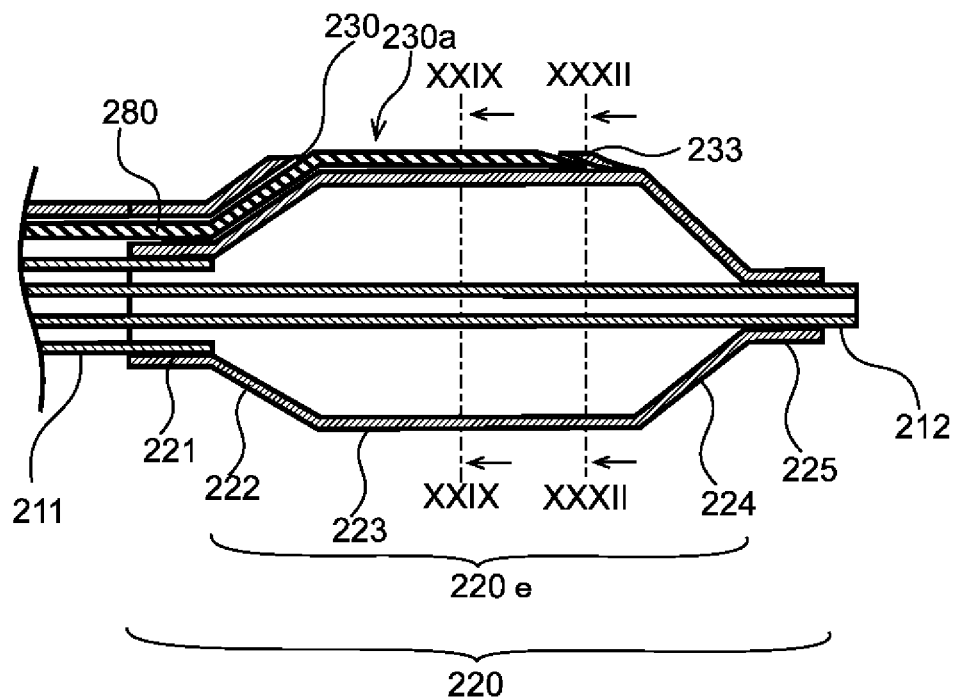

[FIG. 28]
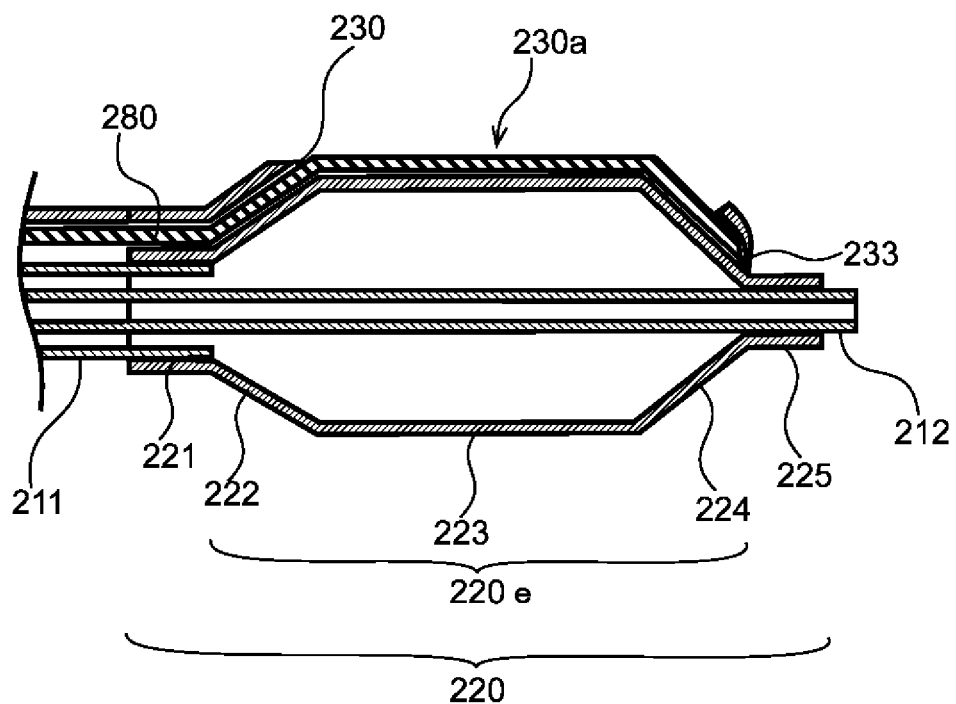
[FIG. 29]
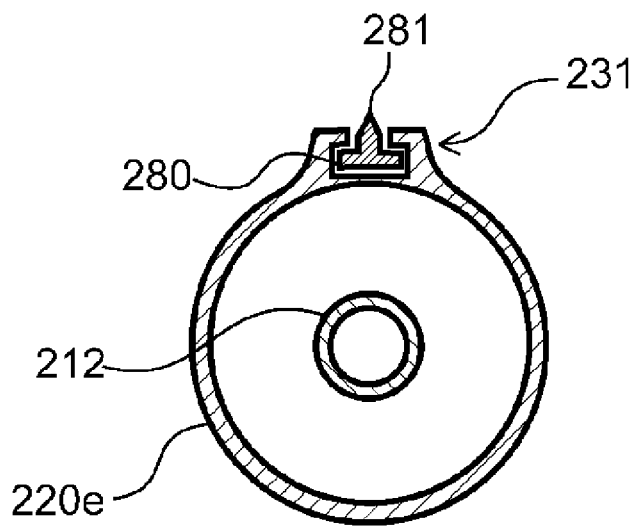

[FIG. 30]
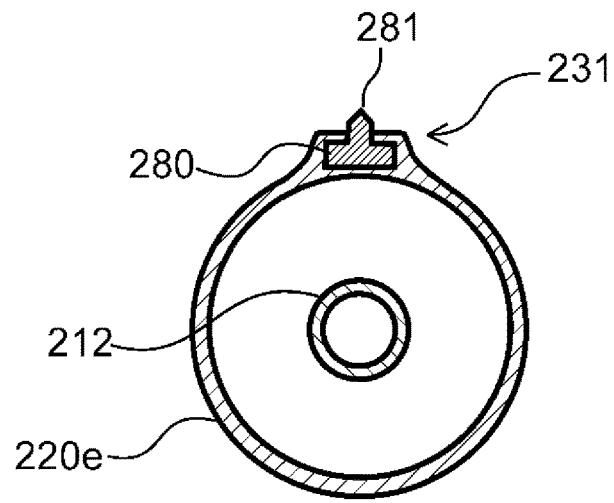
[FIG. 31]
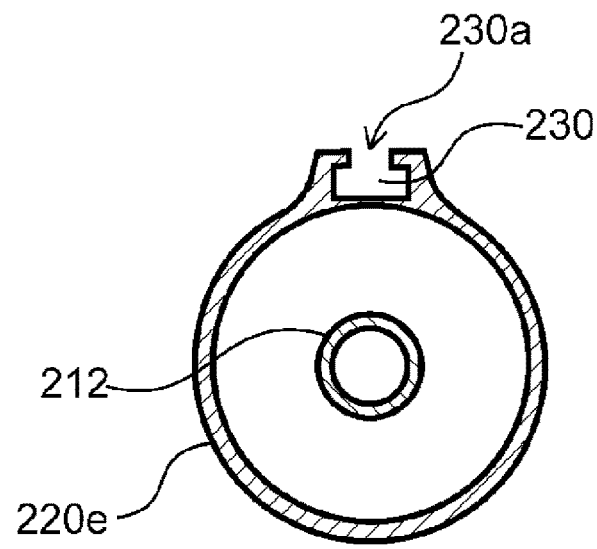
[FIG. 32]
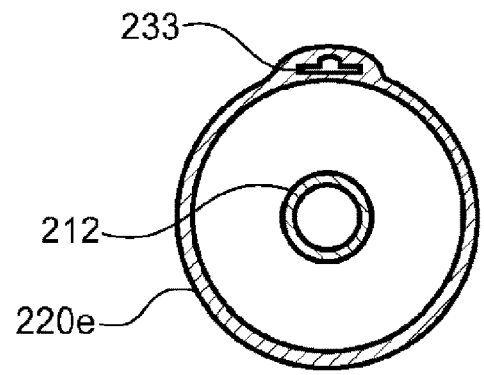

[FIG. 33]
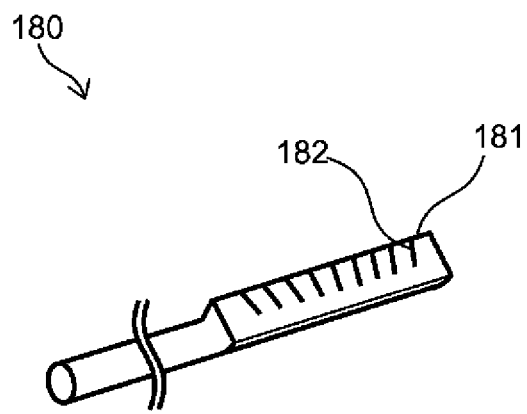
[FIG. 34]
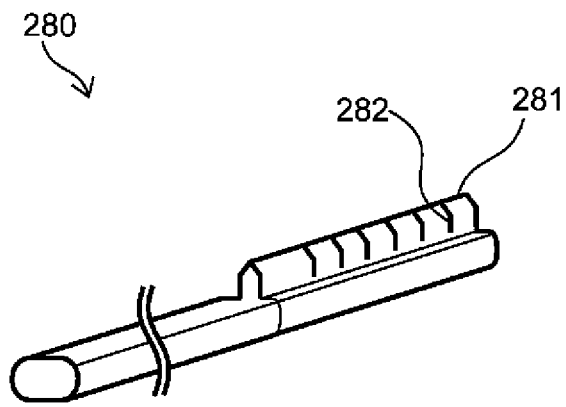

BALLOON CATHETER

CROSS REFERENCE TO RELATED APPLICATIONS

This application is a Continuation of PCT International Application No. PCT/JP2020/046382, filed on Dec. 11, 2020, which claims priority under 35 U.S.C. 119 (a) to Patent Application Nos. 2019-230874, filed in Japan on Dec. 20, 2019 and 2019-230875, filed in Japan on Dec. 20, 2019, all of which are hereby expressly incorporated by reference into the present application.

TECHNICAL FIELD

The present invention relates to a balloon catheter having an elongate body.

BACKGROUND ART

It is known that various diseases occur when blood vessels, which are the channels through which blood circulates in the body, become narrowed and blood circulation is blocked. In particular, stenosis of the coronary arteries that supply blood to the heart can lead to serious diseases such as angina pectoris and myocardial infarction. To treat such stenosis of blood vessels, used is angioplasty procedures, such as percutaneous angioplasty (PTA) and percutaneous coronary angioplasty (PTCA), in which the stenosis is dilated with a balloon catheter. Angioplasty is a minimally invasive therapy that does not require open chest surgery like bypass surgery, and is widely used.

In some cases, hardened stenosis is formed in the inner wall of blood vessels due to calcification. In such a calcified lesion, it is difficult to dilate the hardened stenosis with an ordinary balloon catheter. Another method is to dilate the stenosis by placing an indwelling dilator, called a stent, in the stenotic area of the vessel, however, ISR (In-Stent-Restenosis) may occur after this treatment, in which the neointima of the vessel overgrows and the stenosis occurs again. In ISR lesions, since the neointima is soft and the surface is slippery, a typical balloon catheter may cause the balloon to shift its position away from the lesion during balloon inflation, resulting in damage of the vessel.

A balloon catheter that can dilate the stenosis even in such calcified or ISR lesions is a balloon catheter having a scoring element. The scoring element is a component used to fix the balloon to the inner wall of the vessel wall, crack the calcified area in the inner wall of the vessel wall, or eliminate the stenosis by resecting the calcified area, and usually has a bladed portion for fixation or resection.

For example, there are balloon catheters with such a scoring element, such as those listed in Patent document 1 and Patent document 2. In addition, a balloon catheter with a sheath attached to the balloon with an incising element to protect the incising element when transporting the balloon to the treatment site (Patent document 3), and a balloon catheter with a lumen through which a cutting instrument is passed (Patent document 4) have been disclosed.

RELATED ART DOCUMENT

Patent Document

Patent document 1: JP 2014-506140 T
Patent document 2: JP 2015-104671 A
Patent document 3: JP 2007-512873 T
Patent document 4: JP H9-501852 T

SUMMARY OF THE INVENTION

Problems to be Solved by the Invention

Since the scoring element needs to act on a hard calcified lesion, it is usually formed of a material with high stiffness such as metal. Therefore, if the balloon is inserted into the blood vessel with the scoring element fixed to the balloon from the beginning, the stiffness of the scoring element may deteriorate passage of the balloon in the blood vessel. Accordingly, a method of delivering a long scoring element to the lesion after inserting the balloon into the vessel in a deflated state is sometimes used. In order to fix the blade of the scoring element to the vessel wall or to cut the lesion with the blade, the blade need to contact the vessel wall at a desired angle, however, conventional balloon catheters have a problem that the scoring element rotates axially during delivery, or the scoring element shifts in the circumferential direction of the balloon during delivery, making it impossible to contact the lesion on the inner wall of the vessel at a desired angle.

The present invention has been made in consideration of the above circumstances, and an object of the present invention is to provide a balloon catheter that can make an elongate body contact a lesion at a desired angle by preventing or reducing axial rotation of the elongate body and circumferential shift on the balloon of the elongate body during delivery, while ensuring good passage of the balloon in the blood vessel.

Means for Solving the Problems

An embodiment of a first balloon catheter of the present invention that can solve the above problem has the following configuration.

[1] A balloon catheter, comprising:
a shaft extending in a longitudinal direction from a distal side to a proximal side;
a balloon disposed on a distal side of the shaft;
an elongate body extending along the shaft in the longitudinal direction and having a body tissue contacting part at its distal end part; and
an elongate body lumen through which the elongate body can be passed, wherein
the elongate body and the elongate body lumen are configured so that the elongate body is engaged with an inner wall of the elongate body lumen to form a first engagement part and an axial rotation angle of the elongate body is 0° to 60° at the first engagement part, and
the first engagement part is located at a distal portion of the elongate body lumen between a distal end of the elongate body lumen and a position 30 cm from the distal end of the elongate body lumen toward the proximal side.

In addition, the first balloon catheter of the present invention preferably includes the following [2] to [16].

[2] The balloon catheter according to [1], wherein the elongate body is axially rotatable by 5° to 60° at the first engagement part.

[3] The balloon catheter according to [1] or [2], wherein at the first engagement part, the body tissue contacting part is located at an outer side in a radial direction of the shaft.

[4] The balloon catheter according to any one of [1] to [3], wherein at the first engagement part, a cross-sectional shape of the elongate body perpendicular to the longitudinal direction and a cross-sectional shape of the elongate body lumen perpendicular to the longitudinal direction are non-circular.

[5] The balloon catheter according to any one of [1] to [4], wherein the elongate body has a part having a non-circular shape in cross-section perpendicular to the longitudinal direction between the distal end of the elongate body lumen and the first engagement part, and the elongate body lumen has a part having a circular shape in cross-section perpendicular to the longitudinal direction at a side proximal to the first engagement part.

[6] The balloon catheter according to any one of [1] to [5], wherein the elongate body lumen does not have concave or convex portions extending in a longitudinal axis direction.

[7] The balloon catheter according to any one of [1] to [6], wherein in the longitudinal direction, a cross-sectional shape of the elongate body lumen in a direction perpendicular to the longitudinal direction varies continuously in a section from the first engagement part toward the proximal side.

[8] The balloon catheter according to any one of [1] to [7], wherein the elongate body lumen extends along the shaft so as to be placed at the same position in a radial direction of the shaft.

[9] The balloon catheter according to any one of [1] to [8], wherein the shaft has an inner surface facing inwardly and an outer surface facing outwardly in a radial direction of the shaft, and the elongate body lumen is formed between the inner surface and the outer surface.

[10] The balloon catheter according to any one of [1] to [8], wherein the elongate body lumen is formed as a lumen of a tubular member, and the tubular member and the shaft are joined to each other so that the balloon catheter has the elongate body lumen.

[11] The balloon catheter according to any one of [1] to [10], wherein the first engagement part is placed at the distal end of the elongate body lumen.

[12] The balloon catheter according to any one of [1] to [11], wherein the balloon has an inflating part, and the balloon is fixed to the shaft so that the inflating part is not fixed to the shaft, and the distal end of the elongate body lumen is placed at a position proximal to the inflating part.

[13] The balloon catheter according to any one of [1] to [11], wherein the balloon has an inflating part comprising a straight tube part, a proximal tapered part placed proximal to the straight tube part, and a distal tapered part placed distal to the straight tube part, and the balloon is fixed to the shaft so that the inflating part is not fixed to the shaft, and the distal end of the elongate body lumen is placed at the proximal tapered part.

[14] The balloon catheter according to any one of [1] to [11], wherein the balloon has an inflating part comprising a straight tube part, a proximal tapered part placed proximal to the straight tube part, and a distal tapered part placed distal to the straight tube part, and the balloon is fixed to the shaft so that the inflating part is not fixed to the shaft, and the distal end part of the elongate body lumen is placed at the straight tube part.

[15] The balloon catheter according to any one of [1] to [14], wherein the distal end of the elongate body has a tapered shape.

[16] The balloon catheter according to any one of [1] to [15], wherein the elongate body is a scoring element.

The present invention also provides a second balloon catheter, and an embodiment of the second balloon catheter has the following configuration.

[17] A balloon catheter, comprising:
a shaft extending in a longitudinal direction from a distal side to a proximal side;
a balloon having an inflating part and disposed on a distal side of the shaft;
an elongate body extending along the shaft and the balloon in the longitudinal direction; and
a lumen, through which the elongate body can be passed, extending along the shaft and the balloon in the longitudinal direction and having a longitudinal opening extending in the longitudinal direction, wherein
the lumen has a proximal end that is provided with an insertion opening for inserting the elongate body and that is located at a proximal part of the shaft,
the balloon is fixed to the shaft so that the inflating part of the balloon is not fixed to the shaft, the longitudinal opening of the lumen is disposed along an outer surface of the inflating part, and a proximal end of the longitudinal opening is located between a proximal end and a distal end of the inflating part;
the lumen having no opening between the proximal end of the lumen and the proximal end of the longitudinal opening,
the elongate body and the lumen are configured so that the elongate body is engaged with a part of the longitudinal opening to prevent the elongate body from rotating by 60° or more in a rotational direction around an axis of the longitudinal direction, and
a width of the longitudinal opening at the engagement part is smaller than a width of the lumen at ½ a depth of the lumen.

In addition, the second balloon catheter of the present invention preferably includes the following [18] to [29].

[18] The balloon catheter according to [17], wherein the elongate body is axially rotatable by 5° to 60° at the engagement part.

[19] The balloon catheter according to [17] or [18], wherein the elongate body is disposed in the lumen so that the elongate body is slidably movable in the lumen.

[20] The balloon catheter according to any one of [17] to [19], wherein the lumen does not have concave or convex portions extending in a longitudinal axis direction.

[21] The balloon catheter according to any one of [17] to [20], wherein in the longitudinal direction, a cross-sectional shape of the lumen in a direction perpendicular to the longitudinal direction of the lumen varies continuously in a section from the engagement part toward the proximal side.

[22] The balloon catheter according to any one of [17] to [21], wherein a portion forming the lumen along the balloon is integrally molded with the balloon.

[23] The balloon catheter according to any one of [17] to [22], wherein the inflating part has a straight tube part, a proximal tapered part placed proximal to the straight tube part, and a distal tapered part placed distal to the straight tube part; and the proximal end of the longitudinal opening is placed at the proximal tapered part.

[24] The balloon catheter according to any one of [17] to [22], wherein the inflating part has a straight tube part, a proximal tapered part placed proximal to the straight tube part, and a distal tapered part placed distal to the straight tube part; and the proximal end of the longitudinal opening is placed at the straight tube part.

[25] The balloon catheter according to any one of [17] to [24], wherein the elongate body has a body tissue contacting part, and the lumen and the elongate body are configured so that the lumen and a part of the elongate body other than the body tissue contacting part are engaged with each other at the engagement part.

[26] The balloon catheter according to any one of [17] to [25], wherein the elongate body has a body tissue contacting part, and the body tissue contacting part is located outside the longitudinal opening in a radial direction of the inflating part.

[27] The balloon catheter according to any one of [17] to [26], wherein at a side distal to a distal end of the longitudinal opening, the lumen has a stopper at the same position as a distal end of the elongate body or distal to the distal end of the elongate body.

[28] The balloon catheter according to any one of [17] to [27], wherein one or more incisions are provided in the elongate body placed at the inflating part.

[29] The balloon catheter according to any one of [17] to [28], further comprising a drug inlet provided at a proximal part of the shaft.

Effects of the Invention

According to the balloon catheter of the present invention, the above configuration can prevent or reduce axial rotation of the elongate body and circumferential shift on the balloon of the elongate body during delivery, while ensuring good passage of the balloon in the blood vessel. This makes it possible to properly fix the elongate body to the lesion and to properly resect the lesion with the elongate body.

BRIEF DESCRIPTION OF THE DRAWINGS

FIG. 1 shows an overall view of a first balloon catheter according to an embodiment of the present invention.

FIG. 2 shows a II-II cross-sectional view of the first balloon catheter shown in FIG. 1.

FIG. 3 shows an enlarged cross-sectional view of an elongate body lumen portion of the first balloon catheter shown in FIG. 2.

FIG. 4 shows a cross-sectional view of an elongate body according to an embodiment of the present invention.

FIG. 5 shows a cross-sectional view of an elongate body according to another embodiment of the present invention.

FIG. 6 shows a cross-sectional view of a first balloon catheter according to an embodiment of the present invention.

FIG. 7 shows a VII-VII cross-sectional view of the first balloon catheter shown in FIG. 1.

FIG. 8 shows a side view of a region R of a first balloon catheter according to an embodiment of the present invention.

FIG. 9 shows a side view of a region R of a first balloon catheter according to another embodiment of the present invention.

FIG. 10 shows a side view of a region R of a first balloon catheter according to still another embodiment of the present invention.

FIG. 11 shows a cross-sectional view representing another example of the II-II cross-sectional view of the first balloon catheter shown in FIG. 1.

FIG. 12 shows a cross-sectional view representing still another example of the II-II cross-sectional view of the first balloon catheter shown in FIG. 1.

FIG. 13 shows an overall view of a second balloon catheter according to an embodiment of the present invention.

FIG. 14 shows a plan view of a distal part of the second balloon catheter shown in FIG. 13 viewed from the side of a lumen.

FIG. 15 shows a XV-XV cross-sectional view of the second balloon catheter shown in FIG. 14.

FIG. 16 shows a plan view of a distal part of a second balloon catheter according to another embodiment of the present invention viewed from the side of a lumen.

FIG. 17 shows a XVII-XVII cross-sectional view of the second balloon catheter shown in FIG. 16.

FIG. 18 shows a XVIII-XVIII cross-sectional view of the second balloon catheter shown in FIG. 13.

FIG. 19 shows a XIX-XIX cross-sectional view of the second balloon catheter shown in FIG. 14.

FIG. 20 shows a cross-sectional view representing another example of the XIX-XIX cross-sectional view of the second balloon catheter shown in FIG. 14.

FIG. 21 shows a cross-sectional view representing still another example of the XIX-XIX cross-sectional view of the second balloon catheter shown in FIG. 14.

FIG. 22 shows a XXII-XXII cross-sectional view of the second balloon catheter shown in FIG. 14.

FIG. 23 shows a variation of the XXII-XXII cross-sectional view of the second balloon catheter shown in FIG. 14.

FIG. 24 shows a cross-sectional view of the second balloon catheter shown in FIG. 22 when an elongate body is not inserted.

FIG. 25 shows an enlarged view of a lumen portion of the cross-sectional view shown in FIG. 22.

FIG. 26 shows an enlarged view of a lumen portion of the cross-sectional view shown in FIG. 24.

FIG. 27 shows a cross-sectional view in the longitudinal direction of a distal part of a second balloon catheter according to another embodiment of the present invention.

FIG. 28 shows a cross-sectional view in the longitudinal direction of a distal part of a second balloon catheter according to still another embodiment of the present invention.

FIG. 29 shows a XXIX-XXIX cross-sectional view of the second balloon catheter shown in FIG. 27.

FIG. 30 shows a variation of the XXIX-XXIX cross-sectional view of the second balloon catheter shown in FIG. 27.

FIG. 31 shows a cross-sectional view of the second balloon catheter shown in FIG. 29 when an elongate body is not inserted.

FIG. 32 shows a XXXII-XXXII cross-sectional view of the second balloon catheter shown in FIG. 27.

FIG. 33 shows a perspective view of an elongate body according to an embodiment of the present invention.

FIG. 34 shows a perspective view of an elongate body according to another embodiment of the present invention.

MODE FOR CARRYING OUT THE INVENTION

Hereinafter, the present invention will be described based on the following embodiments, however, the present invention is not limited by the following embodiments, and can be certainly put into practice after appropriate modifications within a range meeting the gist of the above and the below, all of which are included in the technical scope of the present invention. In the drawings, hatching a reference sign for a member may be omitted for convenience, and in such a case, the description and other drawings should be referred to. In addition, sizes of various members in the drawings may differ from the actual sizes thereof, since priority is given to understanding the features of the present invention.

A first balloon catheter according to an embodiment of the present invention has a shaft extending in a longitudinal direction from a distal side to a proximal side; a balloon disposed on a distal side of the shaft; an elongate body extending along the shaft in the longitudinal direction and having a body tissue contacting part at its distal end part; and an elongate body lumen through which the elongate body can be passed, wherein the elongate body and the elongate body lumen are configured so that the elongate body is engaged with an inner wall of the elongate body lumen to form a first engagement part and an axial rotation angle of the elongate body is 0° to 60° at the first engagement part, and the first engagement part is located at a distal portion of the elongate body lumen between a distal end of the elongate body lumen and a position 30 cm from the distal end of the elongate body lumen toward the proximal side. The elongate body lumen having the first engagement part that is engaged with the elongate body so as to prevent a certain range of the axial rotation of the elongate body in the above range allows the elongate body to contact the lesion at a desired angle by preventing or reducing axial rotation of the elongate body and circumferential shift on the balloon of the elongate body.

Hereinafter, a first balloon catheter 100 according to an embodiment of the present invention will be described referring to FIG. 1 to FIG. 12. FIG. 1 shows an overall view of a first balloon catheter 100 according to an embodiment of the present invention. FIG. 2 shows a II-II cross-sectional view of the first balloon catheter 100 shown in FIG. 1, representing a cross-sectional view perpendicular to the longitudinal direction from a distal side to a proximal side at a first engagement part 131. FIG. 3 shows an enlarged cross-sectional view of an elongate body lumen portion of the first balloon catheter 100 shown in FIG. 2. FIG. 4 shows a cross-sectional view of an elongate body according to an embodiment of the present invention, and FIG. 5 shows a cross-sectional view of an elongate body according to another embodiment of the present invention. FIG. 6 shows a cross-sectional view of a first balloon catheter 100 according to an embodiment of the present invention, and FIG. 7 shows a VII-VII cross-sectional view of the first balloon catheter 100 shown in FIG. 1. FIG. 8 to FIG. 10 show a side view of a region R of a first balloon catheter 100 according to another embodiment, respectively. FIG. 11 and FIG. 12 show variations of the II-II cross-sectional view of the first balloon catheter 100 shown in FIG. 1 according to different embodiments, respectively.

As shown in FIG. 1 and FIG. 2, a first balloon catheter 100 has a shaft 110 extending in a longitudinal direction from a distal side to a proximal side, a balloon 120 disposed on a distal side of the shaft 110, an elongate body 180 extending along the shaft 110 in the longitudinal direction and having a body tissue contacting part 181 at is distal end part, and an elongate body lumen 130 through which the elongate body 180 can be passed. The elongate body 180 and the elongate body lumen 130 are configured so that the elongate body 180 is engaged with an inner wall of the elongate body lumen 130 to form a first engagement part 131, and an axial rotation angle of the elongate body 180 is 0° to 60° at the first engagement part 131, and the first engagement part 131 is located at a distal portion of the elongate body lumen 130 between a distal end 130d of the elongate body lumen 130 and a position 30 cm from the distal end 130d of the elongate body lumen 130 toward the proximal side. While the elongate body 180 is exposed from the distal end 130d of the elongate body lumen 130 and is positioned along the balloon 120, the first engagement part 131 disposed in the above range prevents or reduces rotation of the elongate body 180, and makes it unlikely for the elongate body 180 exposed from the distal end 130d of the elongate body lumen 130 to shift in a circumferential direction on the balloon 120, resulting in that the elongate body 180 can be contacted to a lesion at a desired angle.

In the present invention, a distal side refers to the direction towards the person to be treated in the extending direction of the shaft 110, and a proximal side refers to the opposite side of the distal side, that is, the direction towards the user's hand in the extending direction of the shaft 110. The longitudinal direction refers to a direction from the proximal side to the distal side and a direction from the distal side to the proximal side of the shaft 110.

Given that a distance from the distal end 130d of the elongate body lumen 130 to a position where the first engagement part 131 is located is a distance D, the distance D is 0 cm or longer and 30 cm or shorter. This means that the first engagement part 131 may be located at the distal end 130d of the elongate body lumen 130, or may be located anywhere between the distal end 130d of the elongate body lumen 130 and a position 30 cm proximal to the distal end 130d. In addition, the first engagement part 131 may be continuously disposed between the distal end 130d and a position 30 cm proximal to the distal end 130d, or a plurality of the first engagement part 131 may be disposed separately, or only one of the first engagement part 131 may be disposed. The lower limit of the distance D is 0 cm, the upper limit of the distance D is 30 cm, and the distance D may be 25 cm, 20 cm, 15 cm, 10 cm, 5 cm, 3 cm, or 1 cm or shorter. The distance D of the above range can make it possible for the elongate body 180 that is introduced into the elongate body lumen 130 to be unlikely to shift in the circumferential direction on the balloon 120 and to be unlikely to axially rotate even after being exposed from the distal end 130d of the elongate body lumen 130, which makes it possible to contact to a lesion at a desired angle.

As shown in FIG. 2 to FIG. 5, for example, the elongate body 180 has the body tissue contacting part 181 at its distal end part that acts on the living body. The body tissue contacting part 181 can act to a lesion to fix the balloon 120 to the lesion, and can resect a stenosis and the like of the lesion. The body tissue contacting part 181 may have any shape, and for example, preferably has a blade-like shape. The blade-like shape can be formed by processing a part of shapes in a cross-section of the elongate body 180 perpendicular to the longitudinal direction into a blade shape, and the shapes include polygons such as triangles and parallelograms; fans; wedges; convex shapes; spindle shapes; stars; and any combination thereof, or combination the above shape and a circle. FIG. 4 shows a cross-sectional view of the elongate body 180 whose cross-sectional shape is a fan shape, a part of which forming a central angle is processed into a blade part; FIG. 5 shows a cross-sectional view of the elongate body 180 whose cross-sectional shape is a convex shape, a part of which is processed into a blade part. The body tissue contacting part 181 need only be provided at a distal end part of the elongate body 180 that is to be applied to the lesion, and the body tissue contacting part 181 need not be provided on a part of the elongate body 180 other than the distal end part that acts on the lesion.

The cross-sectional shape of a part of the elongate body 180 in which the body tissue contacting part 181 is not provided may be, for example, circular, oval, polygonal, a combination thereof, or any other arbitrary shape, however, a circular shape is preferable. The term "circular" here refers not only to a perfect circle, but also includes all circular shapes. If the cross-sectional shape perpendicular to the longitudinal direction of the part in which the body tissue contacting part 181 is not disposed is circular, it becomes easy to insert the elongate body 180 into the elongate body lumen 130.

A distal end of the elongate body 180 preferably has a tapered shape that tapers off towards the distal end. The distal end of the elongate body 180 having a tapered shape that tapers off towards the distal end makes it easy for the elongate body 180 to be inserted into the elongate body lumen 130.

A major diameter d of a cross-section of the elongate body 180 perpendicular to the longitudinal direction is preferably 0.1 mm or longer, more preferably 0.15 mm or longer, and even more preferably 0.2 mm or longer. The lower limit of the major diameter d of the elongate body 180 within the above range can assure sufficient stiffness to allow the elongate body 180 to act on the lesion. The major diameter d of the elongate body 180 is preferably 1 mm or shorter, more preferably 0.9 mm or shorter, and even more preferably 0.8 mm or shorter. The upper limit of the major diameter d of the elongate body 180 within the above range makes it easy for the elongate body 180 to be inserted into the elongate body lumen 130, which allows the balloon 120 to be delivered to the lesion without deteriorating the insertion of the first balloon catheter 100. As shown in FIG. 4 and FIG. 5, the major diameter is a diameter of a virtual circle inscribed by the cross-section of the elongate body 180 perpendicular to the longitudinal direction, and if the cross-section of the elongate body 180 perpendicular to the longitudinal direction is a circle, the major diameter is the diameter of the circle. Since the elongate body 180 according to an embodiment of the present invention has portions with or without the body tissue contacting part 181, and its cross-sectional shape perpendicular to the longitudinal direction may differ at different locations in the longitudinal direction, the major diameter d may also differ at different locations in the longitudinal direction, however, the major diameter d is preferably within the above range at any cross-section.

The materials constituting the elongate body 180 include, for example, metals such as stainless steel, titanium, nickel-titanium alloys, cobalt-chromium alloys, tungsten alloys; fiber materials made of synthetic resins such as polyarylate fiber, aramid fiber, ultra-high molecular weight polyethylene fiber, PBO fiber, carbon fiber; and ceramics such as alumina, zirconia, barium titanate, and the like. Only one of these materials may be used, or two or more may be used together, and the fiber materials may be monofilaments or multifilaments.

The elongate body lumen 130 may comprise only one lumen as shown in FIG. 2, or may comprise a plurality of lumens, not shown in the figures. The number of the elongate body lumen 130 is 1 or more, and may be 2 or more, and 3 or more. The number of the elongate body lumen 130 is preferably 6 or less, more preferably 5 or less, and even more preferably 4 or less. The number of the elongate body lumen 130 within the above range allows a plurality of the elongate body 180 to be inserted to effectively perform procedures such as fixation and resection without deteriorating the intravascular insertion of the first balloon catheter 100.

A cross-sectional shape of the elongate body lumen 130 other than the first engagement part 131 perpendicular to the longitudinal direction can be any shape as long as the elongate body 180 can be inserted, and may be, for example, a circle, oval, polygon, a combination thereof, or any other arbitrary shape, however, a circle is preferable. If the cross-sectional shape of the elongate body lumen 130 perpendicular to the longitudinal direction is a circle, it is easier to insert the elongate body 180. Here, the term "circle" does not refer only to a perfect circle, but include all circular shapes, as described above.

A major diameter of a cross-section of the elongate body lumen 130 perpendicular to the longitudinal direction is preferably 0.2 mm or longer, more preferably 0.3 mm or longer, and even more preferably 0.5 mm or longer. The lower limit of the major diameter of the elongate body lumen 130 within the above range allows the elongate body 180 to be easily inserted into the elongate body lumen 130. The major diameter of a cross-section of the elongate body lumen 130 perpendicular to the longitudinal direction is preferably 1.2 mm or shorter, more preferably 1 mm or shorter, and even more preferably 0.8 mm or shorter. The upper limit of the major diameter of the elongate body lumen 130 within the above range allows the balloon 120 to be delivered to the lesion without deteriorating the insertion of the first balloon catheter 100. Similar to the major diameter d of the elongate body 180, the major diameter of a cross-section of the elongate body lumen 130 perpendicular to the longitudinal direction is a diameter of a virtual circle inscribed by the cross-section of the elongate body lumen 130 perpendicular to the longitudinal direction, and if the cross-section of the elongate body lumen 130 perpendicular to the longitudinal direction is a circle, the major diameter is the diameter of the circle. The elongate body lumen 130 according to an embodiment of the present invention may have a cross-sectional shape perpendicular to the longitudinal direction that differs at different locations in the longitudinal direction, however, the major diameter is preferably within the above range at any cross-section.

In a preferable embodiment, the elongate body 180 is slidably movable in the elongate body lumen 130. If the elongate body 180 is slidably movable in the elongate body lumen 130, the elongate body 180 can be delivered to the lesion without deteriorating the intravascular insertion of the balloon 120 due to the stiffness of the elongate body 180 by inserting the elongate body 180 into the elongate body lumen 130 after the first balloon catheter 100 arrives at the lesion.

At the first engagement part 131, the elongate body lumen 130 and the elongate body 180 are engaged with each other so as to prevent rotation of the elongate body 180. Here, the engagement of the elongate body lumen 130 and the elongate body 180 to prevent rotation of the elongate body 180 means that the elongate body lumen 130 restricts the movement of the elongate body 180 so as to prevent the rotation about its longitudinal axis, however, it includes not only cases where the elongate body lumen 130 and the elongate body 180 are fixed to each other to completely prevent any rotation, but also cases where the elongate body lumen 130 restricts the movement of the elongate body 180 to the extent that the elongate body 180 has some play in the direction of rotation with the longitudinal axis. As shown in FIG. 3, an angle θ of the play in the rotation direction can be determined by measuring how much the line connecting the body tissue contacting part 181 and the center of gravity of the elongate body 180 rotates axially in the axial direction of the elongate body 180. The angle θ of the axial rotation of the elongate body 180 at the first engagement part 131 is preferably 60° or less, more preferably 50° or less, even ore preferably 40° or less, particularly preferably 20° or less, and most preferably 0° (i.e., having no play).

In a preferable embodiment, the elongate body 180 is axially rotatable by 5° to 60° at the first engagement part 131. More preferably, the elongate body 180 is axially rotatable by 7° or more, and may be axially rotatable y 10° or more, 12° or more, and 15° or more. If the elongate body 180 is engaged with no play at all (i.e., the angle of axially rotation of 0°) at the first engagement part 131, it may become difficult for the elongate body 180 to be inserted into the elongate body lumen 130 that is placed in the living body lumen. Especially, in the bends of the body lumen, the elongate body 180 may become difficult to progress, and in the worst case, the engagement becomes disengaged, making it difficult to control the axial rotation of the elongate body 180. On the other hand, the rotatable angle of the elongate body 180 at the first engagement part 131 within the above range allows its easy insertion into the body lumen while controlling the axial rotation of the elongate body 180, which allows the elongate body 180 to be easily inserted without disengagement even at bends in the body lumen.

The number of the first engagement part 131 may be one, or two or more, and may be continuously formed so that the first engagement part 131 has a certain length or more in the longitudinal direction. The total length of the first engagement part 131 in the longitudinal direction is preferably 2 mm or longer, more preferably 5 mm or longer, and even more preferably 10 mm or longer. The first engagement part 131 having the lower limit of the total length in the longitudinal direction within the above range can prevent the rotation of the elongate body 180 by the engagement of the elongate body lumen 130 and the elongate body 180 with the first engagement part 131, which result in that the elongate body 180 introduced from the first engagement part 131 to the distal side and exposed from the distal end 130d of the elongate body lumen 130 can be brought into contact with the lesion at a desired angle. The upper limit of the total length of the first engagement part 131 in the longitudinal direction is not limited as long as it is within the range of the above distance D, and for example, it may be 200 mm or shorter, 100 mm or shorter, and 50 mm or shorter. The first engagement part 131 having the upper limit of the total length in the longitudinal direction within the above range can prevent the rotation of the elongate body 180 without deteriorating the insertion of the elongate body 180 into the elongate body lumen 130, and also prevent the elongate body 180 introduced from the first engagement part 131 to the distal side and exposed from the distal end 130d of the elongate body lumen 130 from shifting on the balloon 120 in the circumferential direction, which results in that the elongate body 180 can be brought into contact with the lesion t a desired angle.

As shown in FIG. 2, at the first engagement part 31, the body tissue contacting part 181 of the elongate body 180 is preferably located at an outer side in a radial direction of the shaft 110. Here, locating the body tissue contacting part 181 at an outer side in a radial direction of the shaft 110 means that when the concentric circle of the shaft passing the center of gravity of the elongate body 180 is a virtual circle C, the body tissue contacting part 181 is positioned outside the virtual circle C. If the body tissue contacting part 181 is located at an outer side in the radial direction of the shaft 110 at the first engagement part 131, it becomes easier to guide the elongate body 180 introduced from the first engagement part 131 to the distal side and exposed from the distal end 130d of the elongate body lumen 130, with the body tissue contacting part 181 facing outward, making it easier to bring the body tissue contacting part 181 into contact with the lesion. While FIG. 2 shows an embodiment in which the body tissue contacting part 181 is located on the outermost side in the radial direction of the shaft 110, it need not be the outermost side as long as the body tissue contacting part 181 is located outside the above virtual circle C, it can be positioned at a desired angle depending on the target lesion. In a preferable embodiment, the blade-shaped body tissue contacting part 181 located at an outer side in a radial direction of the shaft 110 at the first engagement part 131 allows the elongate body 180 to be guided into the balloon 120 so that it contacts the outer surface of the balloon 120 at a portion other than the body tissue contacting part 181, thereby making it easier to prevent circumferential shift on the balloon 120.

At the first engagement part 131, a cross-sectional shape of the elongate body 180 perpendicular to the longitudinal direction and a cross-sectional shape of the elongate body lumen 130 perpendicular to the longitudinal direction are preferably non-circular. Both the cross-sectional shape perpendicular to the longitudinal direction of the elongate body 180 and the elongate body lumen 130 of non-circular allows the elongate body 180 and the elongate body lumen 130 to be engaged with each other. The term "non-circular" here refers to a shape other than a circular shape given that the circular shape includes not only a perfect circle but also other circle-like shapes.

In the examples shown in FIG. 2 and FIG. 3 at the first engagement part 131, the elongate body lumen 130 having a cross-sectional shape perpendicular to the longitudinal direction of a triangle and the elongate body 180 having a cross-sectional shape perpendicular to the longitudinal direction of a fan shape allow the elongate body lumen 130 and the elongate body 180 to be engaged with each other. In addition to the fan shape in the above example, the cross-sectional shape perpendicular to the longitudinal direction of the elongate body 180 at the first engagement part 131 may be any shape such as polygon including triangle and parallelogram, wedge, convex, spindle, star, and a combination thereof, or it may be a non-circular shape that is a combination of these shapes and a circle. The cross-sectional shape of the elongate body lumen 130 perpendicular to the longitudinal direction may be any non-circular shape as long as it can engage the elongate body 180 having the above cross-sectional shape.

The elongate body 180 preferably has a part having a cross-sectional shape perpendicular to the longitudinal direction of non-circular at a side distal to the first engagement part 131, and the elongate body lumen 130 preferably has a part having a cross-sectional shape perpendicular to the longitudinal direction of circular at a side proximal to the first engagement part 131. As shown in FIG. 6, if the cross-sectional shape of the elongate body 180 at a side distal to the first engagement part 131 is non-circular and the cross-sectional shape of the elongate body lumen 130 at side proximal to the first engagement part 131 is circular, a gap can be easily created between the elongate body 180 and the inner wall of the elongate body lumen 130 when the elongate body 180 is inserted into the elongate body lumen 130, making it easier to insert the elongate body 180 into the elongate body lumen 130.

In a preferable embodiment, the elongate body lumen 130 does not have concave or convex portions extending in the longitudinal axis direction in the lumen. In other words, preferably, the elongate body lumen 130 does not have, for example, a recess into which a protrusion formed in the elongate body 180 enters or a convex portion that enters a groove formed in the elongate body 180 as a means of forming the first engagement part 131. The elongate body lumen 130 not having concave or convex portions extending in the longitudinal axis direction in the lumen allows the elongate body 180 to be easily inserted into the elongate body lumen 130, and also provide the first engagement part 131. This allows the elongate body 180 to be axially rotatable within a range of 60° or less, allowing the elongate body 180 to be flexibly inserted into the elongate body lumen 130 even in tortuous body lumens.

In a preferable embodiment, in the longitudinal direction, the cross-sectional shape of the elongate body lumen 130 perpendicular to the longitudinal direction varies continuously in a section from a position proximal to the first engagement part 131 to the first engagement part 131. As shown in FIG. 7, showing a VII-VII cross-sectional view in FIG. 1, it is preferable because if the cross-sectional shape of the elongate body lumen 130 continuously changes from a position proximal to the first engagement part 131 to the shape of the first engagement part 131 shown in FIG. 2, the axial rotation is gradually restricted in the process of guiding the elongate body 180 to the first engagement part 131 and the elongate body 180 is easily engaged with the elongate body lumen 130 at the first engagement part 131.

The elongate body lumen 130 preferably extends along the shaft 110 so as to be placed at the same position in the radial direction of the shaft 110. If the elongate body lumen 130 extends along the shaft 110 not being placed at the same position in the radial direction of the shaft 110, i.e., the elongate body lumen 130 extends in the extending direction of the shaft 110 along or floating on the shaft 110, operability may be deteriorated when the balloon catheter 100 is twisted or curved. On the other hand, the elongate body lumen 130 extending along the shaft 110 at the same position in the radial direction of the shaft 110, i.e., the elongate body lumen 130 extending in the extending direction of the shaft 110 not floating from the shaft 110 allows easy operation even when the balloon catheter 100 is twisted or curved.

In a preferable embodiment, the shaft 110 has an inner surface facing inwardly and an outer surface facing outwardly in the radial direction of the shaft 110, and the elongate body lumen 130 is formed between the inner surface and the outer surface. FIG. 11 and FIG. 12 show examples in which the shaft 110 has an outer tube 111 and an inner tube 112, and the elongate body lumen 130 is formed between the inner surface and the outer surface of the outer tube 111. Such elongate body lumen 130 can be manufactured by integrally molding the shaft 110 and the elongate body lumen 130. As shown in FIG. 11, the elongate body lumen 130 may be formed outside the shaft 110 in the radial direction. The elongate body lumen 130 formed outside the shaft 110 in the radial direction allows the elongate body 180 to be inserted outwardly in the radial direction, making it easier to be exposed from the distal end 130d of the elongate body lumen 130. Alternatively, as shown in FIG. 12, the elongate body lumen 130 may be formed so that at least a part of it is formed outside the shaft 110 in the radial direction and the rest is formed inwardly in the radial direction of the shaft 110. Thereby, the total diameter of the shaft 110 and the elongate body lumen 130 can be kept small, which improves intravascular insertion. In addition, if the elongate body lumen 130 is formed between the inner and outer surface of the shaft 110 in this way, it becomes easy to extend the elongate body lumen 130 along the shaft 110 so that the elongate body lumen 130 is placed at the same position in the radial direction of the shaft 110.

Alternatively, the elongate body lumen 130 may be formed as a lumen of a tubular member, and the tubular member and the shaft 110 are preferably joined to each other so that the balloon catheter 100 has the elongate body lumen 130. FIG. 2 shows an example in which the elongate body lumen 130 is formed by a tubular member and the tubular member is joined to the shaft 110. If the elongate body lumen 130 is formed as a lumen of a tubular member, the tubular member can be manufactured separately from the shaft 110, making it relatively easy to manufacture the elongate body lumen 130 no matter what the shape it has. The materials constituting the tubular member can be referred to the materials constituting the shaft 110 described above, and may be the same as or different from the materials constituting the shaft 110. The tubular member may be joined to the shaft 110 by existing method such as adhesive bonding and welding.

The first engagement part 131 is preferably placed at the distal end 130d of the elongate body lumen 130. The first engagement part 131 placed at the distal end 130d of the elongate body lumen 130 prevent the elongate body 180 from rotating at a position where it is exposed from the elongated body lumen 130, making it easier for the elongate body 180 to remain in the same posture after it is exposed from the elongate body lumen 130, and thus, it becomes unlikely for the exposed elongate body 180 to axially rotate or shift in the circumferential direction of the balloon 120.

In a preferable embodiment, the balloon 120 has an inflating part 120e that is not fixed to the shaft 110, and fixed parts 120f that are located distal and proximal to the inflating part 120e and connected to the shaft 110, and as shown in FIG. 8, the distal end 130d of the elongate body lumen 130 is placed proximal to the inflating part 120e. In this specification, while there may be a portion that is nether inflating nor fixed between the inflating part 120e and the distal and proximal fixing parts 120f, the portion is included in the fixed part 120f. The distal end 130d of the elongate body lumen 130 located proximal to the inflating part 120e allows the elongate body 180 to be exposed along the inflating part 120e and act on the lesion. While FIG. 8 shows an example in which the first engagement part 131 is located at a position of the shaft 110 along a part where the fixed part 120f is not located in the longitudinal direction of the elongate body lumen 130, the first engagement part 131 may be located at a position of the shaft 110 along a part where the fixed part 120f is located in the longitudinal direction of the elongate body lumen 130, or may be located at the distal end 130d, as long as the distance D is within the above range.

In another preferable embodiment, the inflating part 120e has a straight tube part 122, a proximal tapered part 121 placed proximal to the straight tube part 122, and a distal tapered part 123 placed distal to the straight tube part 122, and as shown in FIG. 9, the distal end 130d of the elongate body lumen 130 is placed in the proximal tapered part 121. The proximal tapered part 121 and the distal tapered part 123 are preferably formed so that the diameter decreases as it is away from the straight tube part 122. The straight tube part 122 of the balloon 120 ensures that there is sufficient contact with the lesion in the straight tube part 122 where the balloon 120 can expand most radially, making it easier to dilate the stenosis and the like in the lesion. By placing the distal end 130d of the elongate body lumen 130 in the proximal tapered part 121, the elongate body 180 can be exposed while preventing axial rotation in the region from the proximal tapered part 121 to the straight tube part 122 that can expand most radially and provide sufficient contact area with the lesion, and the effect of preventing circumferential shift of the elongate body 180 on the balloon 120 is also improved, thus enabling effective treatment of the lesion. While FIG. 9 shows an example in which the first engagement part 131 is located at a position of the elongate body lumen 130 along the proximal tapered part 121 in the longitudinal direction, the first engagement part 131 may be located at a position of the shaft 110 along a part where the fixed part 120f is located, may be located at a position of the shaft 110 along a part where the fixed part 120f is not located, or may be located at the distal end 130d, as long as the distance D is within the above range.

As shown in FIG. 10, the distal end 130d of the elongate body lumen 130 may be located in the straight tube part 122. By placing the distal end 130d of the elongate body lumen 130 in the straight tube part 122, the elongate body 180 can be exposed from the distal end 130d of the elongate body lumen 130 while preventing axial rotation in the straight tube part 122 that can expand most radially and provide sufficient contact area with the lesion, and the effect of preventing circumferential shift of the elongate body 180 on the balloon 120 is also further improved, thus enabling effective treatment of the lesion. While FIG. 9 shows an example in which the first engagement part 131 is located at a position of the elongate body lumen 130 along the straight tube part 122, the first engagement part 131 may be, as described above, located at any position in the longitudinal direction of the elongate body lumen 130, as long as the distance D is within the above range.

The proximal tapered part 121 and the distal tapered part 123 that are formed in the balloon 120 so that the diameter decreases as it is away from the straight tube part 122 can make the outer diameter of the proximal and distal ends of the balloon 120 smaller when the balloon 120 is deflated and wrapped around the shaft 110, reducing the step between the shaft 110 and the balloon 120, which makes it easier to insert the balloon 120 into vessels.

While FIG. 1 shows an example of the so-called over-the-wire type first balloon catheter 100, in which a guidewire that guides the progress of the first balloon catheter 100 is inserted from the distal side to the proximal side of the shaft 110, the first balloon catheter 100 of the present invention can be also applicable to the so-called rapid-exchange type balloon catheter, in which a guidewire is inserted from the distal side to the midway of the proximal side of the shaft 110.

The first balloon catheter 100 is configured so that fluid is supplied to the interior of the balloon 120 through the shaft 110, and the inflation and deflation of the balloon 120 can be controlled using an indeflator (pressurizer for the balloon). The fluid may be a pressure fluid pressurized by a pump or the like.

The shaft 110 is provided with a fluid channel inside. Preferably, the shaft 110 is also provided with a guidewire insertion channel inside. Examples in which the shaft 110 has the fluid channel and the guidewire insertion channel inside are shown in FIG. 1, FIG. 2, and FIG. 6 to FIG. 12, showing a configuration where the shaft 110 has the outer tube 111 and the inner tube 112, the inner tube 112 functions as the guidewire insertion channel, and the space between the inner tube 112 and the outer tube 111 functions as the fluid channel. In the case where the shaft 110 has the outer tube 111 and the inner tube 112, the inner tube 112 preferably extends from the distal end of the outer tube 111 and penetrates the balloon 120 in the longitudinal direction, with the proximal side of the balloon 120 fixed to the outer tube 111 and the distal side of the balloon 120 fixed to the inner tube 112.

The materials constituting the shaft 110 include, for example, polyamide-based resin, polyester-based resin, polyurethane-based resin, polyolefin-based resin, fluorine-based resin, vinyl chloride-based resin, silicone-based resin, and natural rubber. Only one of these materials may be used, or two or more may be used together. Of these, the material constituting the shaft 110 is preferably at least one of polyamide-based resin, polyolefin-based resin, and fluorine-based resin. The shaft 110 made of at least one of polyamide-based resin, polyolefin-based rein, and fluorine-based resin can improve slipperiness of the surface of the shaft 110, which improves the passage of the first balloon catheter 100 into the vessel.

The material constituting the balloon 120 may be at least one selected from the group consisting of polyamide-based resin, polyester-based resin, polyurethane-based resin, polyolefin-based resin, vinyl chloride-based resin, silicone-based resin, and natural rubber. Of these, at least one selected from the group consisting of polyamide-based resin, polyester-based resin, and polyurethane-based resin is preferable. As these resins, elastomer resin may be used.

The balloon 120 can be manufactured by molding the resin. For example, the balloon 120 can be manufactured by placing a resin tube extruded by extrusion molding in a mold, and biaxially stretch blow molding. Alternatively, the balloon 120 can be manufactured by dip molding, injection molding, compression molding, and other known molding methods.

The dimensions of the balloon 120 are preferably 5 mm to 300 mm in length in the longitudinal direction, and 0.5 mm to 12 mm in outer diameter when the lesion is in a blood vessel; the dimensions of the balloon 120 are preferably 10 mm to 100 mm in length in the longitudinal direction, and 3 mm to 30 mm in outer diameter when the lesion is in gastrointestinal tracts, such as the duodenal papilla.

Fixation of the shaft 110 and the balloon 120 may be done, for example, by adhesive bonding, welding, and attaching a ring-shaped member to the overlapping point of the ends of the shaft 110 and the balloon 120 to swage them. Of these, the shaft 110 and the balloon 120 are preferably fixed by welding. The welding of the shaft 110 and the balloon 120 prevents the shaft 110 and the balloon 120 from becoming detached even when the balloon 120 is repeatedly inflated and deflated, easily increasing the strength of the fixation between the shaft 110 and the balloon 120.

To introduce fluid into the shaft 110, the first balloon catheter 100 may have a hub 104 at a proximal side of the shaft 110. The hub 104 preferably has a fluid inlet 106 that is connected to the flow channel of the fluid supplied to the interior of the balloon 120, and a guidewire insertion portion 105 that is connected to the guidewire insertion channel. The first balloon catheter 100 having the hub 104 provided with the fluid inlet 106 and the guidewire insertion portion 105 can facilitate the operation of supplying fluid inside the balloon 120 to inflate and deflate the balloon 120 and delivering the first balloon catheter 100 to a lesion site along a guidewire.

Fixation of the shaft 110 and the hub 104 may be, for example, adhesive bonding and welding. Of these, the shaft 110 and the hub 104 are preferably fixed by adhesive bonding. The adhesive bonding of the shaft 110 and the hub 104 can increase the fixing strength of the shaft 110 and the hub 104 to increase the durability of the first balloon catheter 100 in the case where the material constituting the shaft 110 and the material constituting the hub 104 are different, for example, in which the shaft 110 is made of flexible material and the hub 104 is made of rigid material.

Next, a second balloon catheter according to an embodiment of the present invention will be described. The second balloon catheter according to an embodiment of the present invention has a shaft extending in a longitudinal direction from a distal side to a proximal side; a balloon having an inflating part and disposed on a distal side of the shaft; an elongate body extending along the shaft and the balloon in the longitudinal direction; and a lumen, through which the elongate body can be passed, extending along the shaft and the balloon in the longitudinal direction and having a longitudinal opening extending in the longitudinal direction, wherein the lumen has a proximal end that is provided with an insertion opening for inserting the elongate body and that is located at a proximal part of the shaft, the balloon is fixed to the shaft so that the inflating part of the balloon is not fixed to the shaft, the balloon has a proximal fixed part that is located proximal to the inflating part and connected to the shaft, and the balloon has a distal fixed part that is located distal to the inflating part and connected to the shaft, the longitudinal opening of the lumen is disposed along an outer surface of the inflating part, and a proximal end of the longitudinal opening is located between a proximal end and a distal end of the inflating part; and the lumen has no opening between the proximal end of the lumen and the proximal end of the longitudinal opening, the elongate body and the lumen are configured so that the elongate body is engaged with a part of the longitudinal opening to prevent the elongate body from rotating by 60° or more in a rotational direction around an axis of the longitudinal direction, and a width of the longitudinal opening at the engagement part is smaller than a width of the lumen at ½ a depth of the lumen. This configuration enables the elongate body to be delivered in place by preventing or reducing axial rotation of the elongate body and circumferential shift on the balloon of the elongate body, making it possible for the elongate body to be brought into contact with the lesion at a desired angle, while maintaining good insertion of the balloon in the blood vessel.

Hereinafter, a second balloon catheter 200 according to an embodiment of the present invention will be described referring to FIG. 13 to FIG. 34. FIG. 13 shows an overall view of a second balloon catheter 200 according to an embodiment of the present invention. FIG. 14 shows a plan view of a distal part of the second balloon catheter 200 shown in FIG. 13 seeing from the side of a lumen. FIG. 15 shows a XV-XV cross-sectional view of the second balloon catheter 200 shown in FIG. 14. FIG. 16 shows a plan view of a distal part of the second balloon catheter 200 according to another embodiment of the present invention seeing from the side of a lumen. FIG. 17 shows a XVII-XVII cross-sectional view of the second balloon catheter 200 shown in FIG. 16. FIG. 18 shows a XVIII-XVIII cross-sectional view of the second balloon catheter 200 shown in FIG. 13, representing a cross-sectional view perpendicular to the longitudinal direction of a part where the lumen is disposed along the shaft. FIG. 19 shows a XIX-XIX cross-sectional view of the second balloon catheter 200 shown in FIG. 14, representing a cross-sectional view perpendicular to the longitudinal direction of a part where the lumen does not have the longitudinal opening. FIG. 20 is a cross-sectional view representing another example of the XIX-XIX cross-sectional view of the second balloon catheter 200 shown in FIG. 14. FIG. 21 is a cross-sectional view representing still another example of the XIX-XIX cross-sectional view of the second balloon catheter 200 shown in FIG. 14. FIG. 22 shows a XXII-XXII cross-sectional view of the second balloon catheter 200 shown in FIG. 14, representing a cross-sectional view perpendicular to the longitudinal direction of a part where the lumen has the longitudinal opening. FIG. 23 shows a variation of the XXII-XXII cross-sectional view of the second balloon catheter 200 shown in FIG. 14. FIG. 24 shows a cross-sectional view perpendicular to the longitudinal direction when the elongate body is not pass through the second balloon catheter 200 shown in FIG. 22. FIG. 25 shows an enlarged cross-sectional view of a lumen part of the cross-sectional view shown in FIG. 22, representing a situation where there is play in the engagement between the lumen and the elongate body. FIG. 26 shows an enlarged cross-sectional view of a lumen part of the cross-sectional view shown in FIG. 24. FIG. 27 shows a cross-sectional view perpendicular to the longitudinal direction of the second balloon catheter 200 according to another embodiment of the present invention, and FIG. 28 shows a cross-sectional view perpendicular to the longitudinal direction of the second balloon catheter 200 according to still another embodiment of the present invention. FIG. 29 shows a XXIX-XXIX cross-sectional view of the second balloon catheter 200 shown in FIG. 27, and FIG. 30 shows a variation of the XXIX-XXIX cross-sectional view of the second balloon catheter 200 shown in FIG. 27. FIG. 31 shows a cross-sectional view when the elongate body is not pass through the second balloon catheter 200 shown in FIG. 29. FIG. 32 shows a XXXII-XXXII cross-sectional view of the second balloon catheter 200 shown in FIG. 27. FIG. 33 shows a perspective view of the elongate body according to an embodiment of the present invention, and FIG. 34 shows a perspective view of the elongate body according to another embodiment of the present invention.

As shown in FIG. 13 to FIG. 17, the second balloon catheter 200 has a shaft 210 extending in the longitudinal direction from a distal side to a proximal side; a balloon 220 having an inflating part 220e and disposed on a distal side of the shaft 210; an elongate body 280 extending along the shaft 210 and the balloon 220 in the longitudinal direction; and a lumen 230, through which the elongate body 280 can be passed, extending along the shaft 210 and the balloon 220 in the longitudinal direction and having a longitudinal opening 230a extending in the longitudinal direction, wherein the lumen 230 has a proximal end that is provided with an insertion opening 234 for inserting the elongate body 280 and that is located at a proximal part of the shaft 210, the balloon 220 is fixed to the shaft 210 so that the inflating part 220e of the balloon 220 is not fixed to the shaft 210, the balloon 220 has a proximal fixed part 221 that is located proximal to the inflating part 220e and connected to the shaft 210, and the balloon 220 has a distal fixed part 225 that is located distal to the inflating part 220e and connected to the shaft 210, the longitudinal opening 230a of the lumen 230 is disposed along an outer surface of the inflating part 220e, and a proximal end of the longitudinal opening 230a is located between a proximal end and a distal end of the inflating part 220e; the lumen 230 has no opening between the proximal end of the lumen 230 and the proximal end of the longitudinal opening 230a, the elongate body 280 and the lumen 230 are configured so that the elongate body 280 is engaged with a part of the longitudinal opening 230a to prevent the elongate body 280 from rotating by 60° or more in a rotational direction around an axis of the longitudinal direction, and as shown in FIG. 26, a width W(La) of the longitudinal opening 230a at the engagement part 231 is smaller than a width W(Ld/2) of the lumen 230 at ½ a depth (Ld) of the lumen 230. Due to this configuration, the second balloon catheter 200 can prevent or reduce axial rotation and circumferential shift on the balloon 220 of the elongate body 280, and thus enables the elongate body 280 to be brought into contact with the lesion at a desired angle.

As same as the above explanation about the first balloon catheter 100, a distal side refers to the direction toward the person to be treated in the extending direction of the shaft 210, and a proximal side refers to the opposite side of the distal side, that is, the direction towards the user's hand in the extending direction of the shaft 210. The longitudinal direction refers to a direction from the proximal side to the distal side and a direction from the distal side to the proximal side of the shaft 210.

As shown in FIG. 13 to FIG. 17, the elongate body 280 extends in the longitudinal direction along the shaft 210 and the balloon 220, and can be passed through the lumen 230. The elongate body 280 may have a body tissue contacting part 281 at its distal end part that acts on the living body, the configuration of which can be understood referring to FIG. 4 and FIG. 5, showing the elongate body 180 of the first balloon catheter 100, and the above description about the elongate body 180. The body tissue contacting part 281 can act to a lesion to fix the balloon 220 to the lesion, and can resect a stenosis and the like of the lesion.

The cross-sectional shape perpendicular to the longitudinal direction of a part of the elongate body 280 where the body tissue contacting part 281 is not provided may be, for example, circular, oval, polygonal, a combination thereof, or any other arbitrary shape, however, a circular shape is preferable. The term "circular" here refers not only to a perfect circle, but also includes all circular shapes. If the cross-sectional shape perpendicular to the longitudinal direction of the part of the elongate body 280 where the body tissue contacting part 281 is not provided is circular, it becomes easy to insert the elongate body 280 into the lumen 230.

FIG. 33 shows a perspective view of the elongate body 280 that has a part where the body tissue contacting part 281 is not provided whose cross-sectional shape perpendicular to the longitudinal direction is circular and that has a part where the body tissue contacting part 281 is provided whose cross-sectional shape perpendicular to the longitudinal direction is fan-like, and FIG. 34 shows a perspective view of the elongate body 280 that has a part where the body tissue contacting part 281 is not provided whose cross-sectional shape perpendicular to the longitudinal direction is oval and that has a part where the body tissue contacting part 281 is provided whose cross-sectional shape perpendicular to the longitudinal direction is convex. As shown in these examples, the cross-sectional shape of the elongate body 280 perpendicular to the longitudinal direction may differ at different locations in the longitudinal direction.

While not shown in the figures, a distal end of the elongate body 280 preferably has a tapered shape that tapers off towards the distal end. The distal end of the elongate body 280 having a tapered shape that tapers off towards the distal end makes it easier for the elongate body 280 to be inserted into the lumen 230, and reduces the risk of injury to biological tissue with the distal end of the elongate body 280 after being delivered to the lesion.

A major diameter d of a cross-section of the elongate body 280 perpendicular to the longitudinal direction is preferably 0.1 mm or longer, more preferably 0.15 mm or longer, and even more preferably 0.2 mm or longer. The lower limit of the major diameter d of the elongate body 280 within the above range can assure sufficient stiffness to allow the elongate body 280 to act on the lesion. The major diameter d of the elongate body 280 is preferably 1 mm or shorter, more preferably 0.9 mm or shorter, and even more preferably 0.8 mm or shorter. The upper limit of the major diameter d of the elongate body 280 within the above range makes it easy for the elongate body 280 to be inserted into the lumen 230, which allows the balloon 220 to be delivered to the lesion without deteriorating the insertion of the second balloon catheter 200. The major diameter is a diameter of a virtual circle inscribed by the cross-section of the elongate body 280 perpendicular to the longitudinal direction, and if the cross-section of the elongate body 280 perpendicular to the longitudinal direction is a circle, the major diameter is the diameter of the circle. Since the elongate body 280 according to an embodiment of the present invention has portions with or without the body tissue contacting part 281, and its cross-sectional shape perpendicular to the longitudinal direction may differ at different locations in the longitudinal direction, the major diameter d may also differ at different locations in the longitudinal direction, however, the major diameter d is preferably within the above range at any cross-section. As for the above explanation, FIG. 4, which shows the elongate body 180 of the first balloon catheter 100, can be referred to.

The materials constituting the elongate body 280 include, for example, metals such as stainless steel, titanium, nickel-titanium alloys, cobalt-chromium alloys, tungsten alloys; fiber materials made of synthetic resins such as polyarylate fiber, aramid fiber, ultra-high molecular weight polyethylene fiber, PBO fiber, carbon fiber; and ceramics such as alumina, zirconia, barium titanate, and the like. Only one of these materials may be used, or two or more may be used together, and the fiber materials may be monofilaments or multifilaments.

The lumen 230 only need to extend along the shaft 210 and the balloon 220 in the longitudinal direction, and especially in the part where extending along the balloon 220, may be disposed straight with no angle to the central axis of the balloon 220, or may be disposed at angle to the central axis of the balloon 220 to be spiraled. The arrangement of the lumen 230 along the balloon 220, such as linear or spiral, can be selected to best suit the lesion to be treated. By inserting the elongate body 280 into the lumen 230, the elongate body 280 can be delivered to a predetermined position while preventing or reducing circumferential shift, and also preventing or reducing axial rotation of the elongate body 280 to contact the lesion at a desired angle.

The proximal end of the lumen 230 is located at a proximal part of the shaft 210, and is provided with an insertion opening 234 for inserting the elongate body 280 as shown in FIG. 13. The elongate body 280 can be introduced from the insertion opening 234 to be inserted into the lumen 230. The elongate body 280 may be disposed in the lumen 230 from the beginning, or may be inserted after the balloon 220 is delivered to the lesion. In addition, the elongate body 280 is preferably slidably movable in the lumen 230. While the elongate body 280 is disposed in order to fix the balloon 220 to the lesion or to resect stenosis and the like generated at the lesion, if the elongate body 280 is slidably movable, the elongate body 280 can be placed at any position in the longitudinal direction. The embodiment where the elongate body 280 is inserted into the lumen 230 after the balloon 220 has been delivered to the lesion is preferable, because the balloon 220 can be easily delivered to the lesion without deteriorating the insertion in blood vessels of the balloon 220 due to the stiffness of the elongate body 280.

The placement of the elongate body 280 in the lumen 230 that extends along the shaft 210 and the balloon 220 allows the elongate body 280 to be guided by the lumen 230, preventing the elongate body 280 from being inserted with unintended shift in the circumferential direction of the shaft 210 and the balloon 220. This allows the elongate body 280 to be delivered to a desired location. Especially, the placement of the elongate body 280 in the lumen 230 along the balloon 220 that is delivered to a lesion can prevent unintended circumferential shift of the elongate body 280 at the lesion site. Here, the circumferential shift of the elongate body 280 on the balloon 220 means that the elongate body 280 travels in an unintended direction on the outer surface of the balloon 220. Therefore, while the lumen 230 disposed at angle to the central axis of the shaft 210 to be spiraled on the balloon 220 makes the elongated body 280 inserted in the lumen 230 travel spirally with respect to the longitudinal direction of the balloon 220, this does not mean that the elongate body 280 shifts in the circumferential direction of the balloon 220. The shift only means that the elongate body 280 travels in an unintended direction.

As shown in FIG. 18 to FIG. 21, The cross-sectional shape perpendicular to the longitudinal direction of a part of the lumen 230 without the longitudinal opening 230a may be circular. The term "circular" here refers not only to a perfect circle, but also includes all circular shapes. Alternatively, the cross-sectional shape of the lumen 230 perpendicular to the longitudinal direction may be oval, polygonal, a combination thereof, or any other arbitrary shape. Especially, as shown in FIG. 18, at a part where the lumen 230 extends along the shaft 210, the cross-sectional shape of the lumen 230 perpendicular to the longitudinal direction is preferably circular. The circular cross-sectional shape of the lumen 230 at a part where it extends along the shaft 210 allows the elongate body 280 to be easily inserted. At a part where the lumen 230 extends along the balloon 220, the cross-sectional shape of the lumen 230 without the longitudinal opening 230a perpendicular to the longitudinal direction may be circular as shown in FIG. 19 to FIG. 21 or any shape described above, or may correspond to the cross-sectional shape of the elongate body 280 placed in the lumen 230. The cross-sectional shape perpendicular to the longitudinal direction of the lumen 230 that corresponds to the cross-sectional shape of the elongate body 280 is preferable, because axial rotation of the elongate body 280 can be prevented to some extent by the lumen 230 along the balloon 220 even at a position without the longitudinal opening 230a.

A major diameter of the cross-section of the lumen 230 perpendicular to the longitudinal direction is preferably 0.2 mm or longer, more preferably 0.3 mm or longer, and even more preferably 0.5 mm or longer. The lower limit of the major diameter of the cross-section of the lumen 230 perpendicular to the longitudinal direction within the above range allows the elongate body 280 to be easily inserted into the lumen 230. The major diameter of the cross-section of the lumen 230 perpendicular to the longitudinal direction is preferably 1.2 mm or shorter, more preferably 1 mm or shorter, and even more preferably 0.8 mm or shorter. The upper limit of the major diameter of the cross-section of the lumen 230 perpendicular to the longitudinal direction within the above range allows the balloon 220 to be delivered to the lesion without deteriorating the insertion of the balloon catheter 200. The major diameter of the cross-section of the lumen 230 perpendicular to the longitudinal direction is, as the same as the major diameter d of the elongate body 280, a diameter of a virtual circle inscribed by the cross-section of the lumen 230 perpendicular to the longitudinal direction, and if the cross-section of the lumen 230 perpendicular to the longitudinal direction is a circle, it is the diameter of the circle. While the lumen 230 according to embodiments of the present invention may have a cross-sectional shape perpendicular to the longitudinal direction that differs at different locations in the longitudinal direction, and the major diameter of the cross-section may also differ, the major diameter is preferably within the above range at any cross-section.

FIG. 19 to FIG. 21 are XIX-XIX cross-sectional views of the second balloon catheter 200 shown in FIG. 14 according to different embodiments respectively, representing a cross-sectional view of a part of the lumen 230 without the longitudinal opening 230a at a part where the lumen 230 extends along the balloon 220. As shown in FIG. 19, the lumen 230 may comprise only one lumen, or may comprise a plurality of lumens as shown in FIG. 20. The number of the lumen 230 is 1 or more, and may be 2 or more, and 3 or more. The number of the lumen 230 is preferably 6 or less, more preferably 5 or less, and even more preferably 4 or less. The number of the lumen 230 within the above range allows a plurality of the elongate body 280 to be inserted to effectively perform procedures such as fixation and resection without deteriorating the intravascular insertion of the second balloon catheter 200.

As shown in FIG. 19 and FIG. 20, the lumen 230 may be formed outside the balloon 220 in the radial direction. The lumen 230 formed outside the balloon 220 in the radial direction allows the introduced elongate body 280, drugs, and the like to be disposed outside the balloon 220 in the radial direction, making it easier to apply the elongate body 280, drugs, and the like to the lesion. Alternatively, as shown in FIG. 21, the lumen 230 may be formed so that at least a part of it is formed outside the balloon 220 in the radial direction and the rest is formed inwardly in the radial direction of the balloon 220. Thereby, the total diameter of the balloon 220 and the lumen 230 can be kept small, which is preferable because it improves intravascular insertion. The above configuration can be also applied to the part of the lumen 230 where it extends along the shaft 210.

The balloon 220 has the inflating part 220e that is not fixed to the shaft 210, the proximal fixed part 221 that is located proximal to the inflating part 220e and connected to the shaft 210, and the distal fixed part 225 that is located distal to the inflating part 220e and connected to the shaft 210, and as shown in FIG. 13 to FIG. 17, the lumen 230 has the longitudinal opening 230a extending in the longitudinal direction at an outward side in the radial direction of the balloon 220 at the inflating part 220e, and the proximal end of the longitudinal opening 230a is located distal to the proximal end of the inflating part 220e. This allows a part of the elongate body 280 to be exposed from the longitudinal opening 230a, and the exposed part of the elongate body 280 can act on the lesion. In this specification, while there may be a portion that is neither inflating nor fixed between the inflating part 220e and the proximal fixed part 221 and between the inflating part 220e and the distal fixed part 225, such a portion is included in the proximal fixed part 221 and the distal fixed part 225.

As show in FIG. 14 and FIG. 15, the distal end of the longitudinal opening 230a may be the distal end 230d of the lumen 230. The distal end 230d of the lumen 230 may have an exit through which the elongate body 280 can be advanced or retracted in the longitudinal direction, and the distal side of the elongate body 280 may be exposed from the exit. Alternatively, as shown in FIG. 16 and FIG. 17, the distal end 230d of the lumen 230 may be placed distal to the distal end of the longitudinal opening 230a. That is, there is a part of the lumen 230 without the opening distal to the distal end of the longitudinal opening 230a, guiding the elongate body 280 through the part to a side distal to the longitudinal opening 230a, and the elongate body 280 may be exposed from the exit disposed at the distal end 230d of the lumen 230. In this embodiment, the distal side of the elongate body 280 can be exposed on the distal portion of the balloon catheter 200, so that the lesion can be treated by creeping forward technique and the like, in which the balloon 220 is repeatedly inflated and deflated while the balloon 220 is advanced to make an incision with the elongate body 280.

The inflating part 220e preferably has a straight tube part 223, a proximal tapered part 222 placed proximal to the straight tube part 223, and a distal tapered part 224 placed distal to the straight tube part 223, and as shown in FIG. 14 to FIG. 17, the proximal end of the longitudinal opening 230a is preferably placed at the proximal tapered part 222. The proximal tapered part 222 and the distal tapered part 224 is preferably formed so that the diameter decreases as it is away from the straight tube part 223. The straight tube part 223 of the balloon 220 ensures that there is sufficient contact with the lesion in the straight tube part 223 where the balloon 220 can expand most radially, making it easier to dilate the stenosis and the like in the lesion. The proximal tapered part 222 and the distal tapered part 224 formed in the balloon 220 so that the diameter decreases as it is away from the straight tube part 223 can make the outer diameter of the proximal and distal ends of the balloon 220 smaller when the balloon 220 is deflated and wrapped around the shaft 210, reducing the step between the shaft 210 and the balloon 220, which makes it easier to insert the balloon 220 into vessels. If the longitudinal opening 230a is located at the proximal tapered part 222, the elongate body 280 can be exposed through the longitudinal opening 230a from the proximal tapered part 222 to the straight tube part 223, resulting in wide range of exposure of the elongate body 280 to efficiently treat the lesion.

While not shown in the figures, the proximal end of the longitudinal opening 230a may be located at the straight tube part 223. This allows the elongate body 280 to be exposed at the straight tube part 223 where the balloon 220 can expand most radially and provide sufficient contact area with the lesion, so that the lesion can be efficiently treated.

The distal end of the longitudinal opening 230a may be located at the straight tube part 223, or may be located at the distal tapered part 224. If the distal end of the longitudinal opening 230a is located at the straight tube part 223, the elongate body 280 can be exposed at the straight tube part 223 where the balloon 220 can expand most radially and provide sufficient contact area with the lesion. If the distal end of the longitudinal opening 230a is located at the distal tapered part 224, the elongate body 280 can be exposed at the distal end part of the balloon 220.

The length of the longitudinal opening 230a in the longitudinal direction is preferably 1/10 the length of the inflating part 220e or longer in the longitudinal direction, more preferably 1/5 or longer, and even more preferably 1/2 or longer. The length of the longitudinal opening 230a in the longitudinal direction is preferably the length of the inflating part 220e in the longitudinal direction or shorter, more preferably 9/10 the length of the inflating part 220e or shorter, even more preferably 4/5 or shorter, or may be 2/3 or shorter. In addition, the longitudinal opening 230a may be disposed continuously in the inflating part 220e, or may be disposed discontinuously. The longitudinal opening 230a having the above range of length in the longitudinal direction with respect to the length of the inflating part 220e in the longitudinal direction allows the elongate body 280 to be exposed through the longitudinal opening 230a to treat the lesion.

The lumen 230 has no opening between the proximal end of the lumen 230 and the proximal end of the longitudinal opening 230a. The lumen 230 having no opening in the above range can prevent the elongate body 280 from being exposed where it is not needed, resulting in protecting the elongate body 280 and preventing living tissue from damaged by the elongate body 280.

The elongate body 280 and the lumen 230 are configured so that the elongate body 280 is engaged with a part of the longitudinal opening 230a at the engagement part 231 to prevent the elongate body 280 from rotating by 60° or more in a rotational direction around an axis of the longitudinal direction. FIG. 22 shows a cross-sectional view perpendicular to the longitudinal direction of the engagement part 231 at which the elongate body 280 is engaged, and FIG. 23 shows a variation of a cross-sectional view perpendicular to the longitudinal direction of the engagement part 231 at which the elongate body 280 is engaged. FIG. 24 shows a cross-sectional view perpendicular to the longitudinal direction of the longitudinal opening 230a at the engagement part 231 shown in FIG. 22, and FIG. 25 shows an enlarged view of the part of the lumen 230 shown in the cross-sectional view of FIG. 22. Here, the engagement of the lumen 230 and the elongate body 280 to prevent rotation of the elongate body 280 means that the lumen 230 restricts the movement of the elongate body 280 so as to prevent the rotation about its longitudinal axis, however, it includes not only cases where the lumen 230 and the elongate body 280 are fixed to each other to completely prevent any rotation as shown in FIG. 23, but also cases where the lumen 230 restricts the movement of the elongate body 280 to the extent that the elongate body 280 has some play in the direction of rotation with the longitudinal axis as shown in FIG. 22 and FIG. 25. In this case, the elongate body 280 is preferably refrained from axially rotating by 60° or more in the rotational direction with the longitudinal axis at the engagement part 231. The axially rotational angle θ of the elongate body 280 can be determined by measuring how much the line connecting one of the points where the elongate body 280 touches the circumscribed circle and the gravity center of the elongate body 280 rotates axially in the axial direction of the elongate body 280. While FIG. 25 shows a case where the one point of the points where the elongate body 280 touches the circumscribed circle is the body tissue contacting part 281, the one point of the points where the elongate body 280 touches the circumscribed circle can be uniquely determined, and therefore, the axially rotational angle θ can be obtained. The axially rotational angle θ of the elongate body 280 at the engagement part 231 is preferably 40° or less, more preferably 20° or less, and most preferably 0° (i.e., having no play).

At the engagement part 231, the elongate body 280 is preferably axially rotatable by 5° to 60°. The elongate body 280 is more preferably axially rotatable by 7° or more, and may be by 10° or more, 12° or more, and 15° or more. If the elongate body 280 is engaged with no play at all (i.e., the axially rotatable angle of 0°) at the engagement part 231, it may become difficult for the elongate body 280 to be inserted into the lumen 230 that is placed in the body lumen. Especially, in the bends of the body lumen, the elongate body 280 may become difficult to progress, and in the worst case, the engagement becomes disengaged, making it difficult to control the axial rotation of the elongate body 280. On the other hand, the rotatable angle of the elongate body 280 at the engagement part 231 within the above range allows its easy insertion into the living body lumen while controlling the axial rotation of the elongate body 280 to make it easily pass through without disengagement even at bends of the body lumen.

The lumen 230 having the engagement part 231 that is engaged with the elongate body 280 at least in a part having the longitudinal opening 230a to prevent the elongate body 280 from rotating can prevent axial rotation of the elongate body 280 at a part where a part of the elongate body 280 is exposed to act on the living tissue, making the elongate body 280 become in contact with the living tissue at a desired angle.

A width W(La) of the longitudinal opening 230a at the engagement part 231 is smaller than a width W(Ld/2) of the lumen 230 at ½ the depth (Ld) of the lumen (Ld/2). FIG. 26 shows an example of the width W(La) of the longitudinal opening 230a of the lumen 230, and the width W(Ld/2) at ½ the depth (Ld) of the lumen (Ld/2).

The engagement part 231 may be formed continuously in the longitudinal direction from the proximal end to the distal end of the longitudinal opening 230a of the lumen 230, or may be formed in a part of the section from the proximal end to the distal end of the longitudinal opening 230a of the lumen 230. In the case where the engagement part 231 is formed in a part of the section from the proximal end to the distal end of the longitudinal opening 230a of the lumen 230, the length of the engagement part 231 in the longitudinal direction is preferably 10% or longer of the length of the longitudinal opening 230a in the longitudinal direction, more preferably 20% or longer, even more preferably 30% or longer, and especially preferably 50% or longer. The above range of the length of the engagement part 231 in the longitudinal direction with respect to the length of the longitudinal opening 230a in the longitudinal direction can prevent axial rotation of the elongate body 280.

As shown in FIG. 22, FIG. 23, and FIG. 25, at the engagement part 231, the lumen 230 and a part of the elongate body 280 other than the body tissue contacting part 281 are preferably engaged with each other. By engaging the part other than the body tissue contacting part 281 with the lumen 230, the body tissue contacting part 281 can be exposed through the longitudinal opening 230a without being interfered by the engagement with the lumen 230, allowing the body tissue contacting part 281 to become in contact with the lesion.

Furthermore, as shown in FIG. 22, FIG. 23, and FIG. 25, the body tissue contacting part 281 is preferably located outside the longitudinal opening 230a in the radial direction of the inflating part 220e. Especially, in the natural state, where no pressure is applied to the balloon 220 and the lumen 230, the body tissue contacting part 281 is preferably located outside the longitudinal opening 230a in the radial direction of the inflating part 220e. In embodiments of the present invention, the elongate body 280 can be delivered to the lesion through the lumen 230 after the balloon 220 has been delivered to the lesion, allowing the procedure to be performed without unnecessarily contacting or damaging the body tissue, even if the body tissue contacting part 281 is located outside the longitudinal opening 230a in the radial direction of the inflating part 220e in the natural state.

The lumen 230 preferably does not have concave or convex portions extending in the longitudinal axis direction. That is, the lumen 230 preferably does not have, for example, concave that a protrusion formed in the elongate body 280 enters or convex that enters a groove formed in the elongate body 280 as a means for forming the engagement part 231. The lumen 230 not having concave or convex extending in the longitudinal axis direction allows the engagement part 231 to be formed while allowing the longitudinal body 280 to be easily inserted in the lumen 230. Thereby, the elongate body 280 can be made rotatable by 60° or less, allowing the elongate body 280 to be flexibly inserted into the lumen 230 even in a bent body lumen.

In the longitudinal direction, the cross-sectional shape of the lumen 230 perpendicular to the longitudinal direction preferably varies continuously in a section from a position proximal to the engagement part 231 to the engagement part 231. If the engagement part 231 is formed by such a continuous change, the axial rotation of the elongate body 280 is gradually controlled in the process of being guided to the engagement part 231, making it easier for the elongate body 280 to be easily engaged with the lumen 230 at the engagement part 231.

Referring to FIG. 27 to FIG. 34, the balloon catheter 200 according to another embodiment of the present invention will be described. As shown in FIG. 27 and FIG. 28, at a side distal to the distal end of the longitudinal opening 230a, the lumen 230 preferably has a stopper 233 at the same position as the distal end of the elongate body 280 or distal to the distal end of the elongate body 280. The stopper 233 disposed at the same position as the distal end of the elongate body 280 or distal to the distal end of the elongate body 280 can prevent the elongate body 280 from travelling distal to the stopper 233, thus preventing the elongate body 280 from acting on unintended parts or damaging the vessel wall and the like.

The stopper 233 may be placed at the straight tube part 223 as shown in FIG. 27, may be placed at the distal tapered part 224 as shown in FIG. 28, or may be placed at the distal fixed part 225 not shown in the figures. Depending on where the stopper 233 is placed and where the distal end of the longitudinal opening 230a is placed, it can be chosen where the elongate body 280 is exposed on the balloon 220. For example, as shown in FIG. 28, if the stopper 233 is placed at the distal tapered part 224 and the distal end of the longitudinal opening 230a is also placed at the distal tapered part 224, the elongate body 280 can be exposed from the straight tube part 223 to the distal tapered part 224, so that the lesion can be treated by creeping forward technique and the like, in which the balloon 220 is repeatedly inflated and deflated while the balloon 220 is advanced to make an incision with the elongate body 280.

The means for providing the stopper 233 is not limited, but for example, it can be formed by crushing the lumen 230 provided as shown in FIG. 31 into the shape as shown in FIG. 32. Crushing the lumen 230 as shown in FIG. 32, the crushed part of the lumen 230 becomes the stopper 233 for the elongate body 280, which prevents the elongate body 280 inserted in the lumen 230 as shown in FIG. 29 and FIG. 30 from traveling distal to it. While FIG. 29 shows an embodiment in which the axial rotation of the elongate body 280 at the engagement part 231 has a play and FIG. 30 shows an embodiment in which the axial rotation of the elongate body 280 at the engagement part 231 has no play, in either embodiment, the stopper 233 can prevent the elongate body 280 from traveling further distal to it.

One or more incisions 282 are preferably provided in the elongate body 280 placed at the inflating part 220e. The incisions 282 can improve the flexibility of the elongate body 280, allowing the elongate body 280 to easily follow the balloon 220. The number of the incisions 282 is preferably 2 or more, more preferably 3 or more, and even more preferably 5 or more; the number of the incisions 282 is preferably 20 or less, more preferably 15 or less, and even more preferably 12 or less. The above range of the number of the incisions 282 can improve the flexibility of the elongate body 280 without compromising its strength.

As shown in FIG. 33 and FIG. 34, the incisions 282 is formed at the side of the elongate body 280 on which the body tissue contacting part 281 is provided. The orientation and size of the incisions 282 are not limited as long as the flexibility of the elongate body 280 can be improved without compromising its strength. The incisions 282 may be provided perpendicular or at an angle other than perpendicular to the axis direction of the elongate body 280, and as shown in FIG. 33, each of the plurality of the incisions 282 may be provided at different angles to the axis direction of the elongate body 280, or each of the plurality of the incisions 282 may be provided at the same angle to the axis direction of the elongate body 280 as shown in FIG. 34. Even if the body tissue contacting part 281 is located outwardly in the radial direction of the inflating part 220e, the incisions 282 provided at the side on which the body tissue contacting part 281 is provided makes it easier to follow the curve of the inflating part 220e.

While FIG. 13 shows an example of the so-called over-the-wire type balloon catheter 200, in which a guidewire that guides the progress of the balloon catheter 200 is inserted from the distal side to the proximal side of the shaft 210, the second balloon catheter 200 of the present invention can be also applicable to the so-called rapid-exchange type balloon catheter, in which a guidewire is inserted from the distal side to the midway of the proximal side of the shaft 210.

The balloon catheter 200 is configured so that fluid is supplied to the interior of the balloon 220 through the shaft 210, and the inflation and deflation of the balloon 220 can be controlled using an indeflator (pressurizer for the balloon). The fluid may be a pressure fluid pressurized by a pump or the like.

The shaft 210 is provided with a fluid channel inside. Preferably, the shaft 210 is also provided with a guidewire insertion channel inside. Examples in which the shaft 210 has the fluid channel and the guidewire insertion channel are shown, for example, in FIG. 13 to FIG. 17, FIG. 27, and FIG. 28, showing a configuration where the shaft 210 has an outer tube 211 and an inner tube 212, the inner tube 212 functions as the guidewire insertion channel, and the space between the inner tube 212 and the outer tube 211 functions as the fluid channel. In the case where the shaft 210 has the outer tube 211 and the inner tube 212, the inner tube 212 preferably extends from the distal end of the outer tube 211 and penetrates the balloon 220 in the longitudinal direction, with the proximal side of the balloon 220 fixed to the outer tube 211 and the distal side of the balloon 220 fixed to the inner tube 212.

The materials constituting the shaft 210 include, for example, polyamide-based resin, polyester-based resin, polyurethane-based resin, polyolefin-based resin, fluorine-based resin, vinyl chloride-based resin, silicone-based resin, and natural rubber. Only one of these materials may be used, or two or more may be used together. Of these, the material constituting the shaft 210 is preferably at least one of polyamide-based resin, polyolefin-based resin, and fluorine-based resin. The shaft 210 made of at least one of polyamide-based resin, polyolefin-based resin, and fluorine-based resin can improve slipperiness of the surface of the shaft 210, which improves the passage of the balloon catheter 200 into the vessel.

The material constituting the balloon 220 may be at least one selected from the group consisting of polyamide-based resin, polyester-based resin, polyurethane-based resin, polyolefin-based resin, vinyl chloride-based resin, silicone-based resin, and natural rubber. Of these, at least one selected from the group consisting of polyamide-based resin, polyester-based resin, and polyurethane-based resin is preferable. As these resins, elastomer resin may be used.

The balloon 220 can be manufactured by molding the resin. For example, the balloon 220 can be manufactured by placing a resin tube extruded by extrusion molding in a mold, and biaxially stretch blow molding. Alternatively, the balloon 220 can be manufactured by dip molding, injection molding, compression molding, and other known molding methods.

In a preferable embodiment, a portion forming the lumen 230 along the balloon 220 is integrally molded with the balloon 220. The lumen 230 integrally molded with the balloon 220 makes it easier to manufacture the lumen 230. The methods of integrally molding the portion forming the lumen 230 with the balloon 220 include, for example, the one in which the balloon 220 is manufactured by the above extrusion molding and the like, while securing the lumen with a core material for the lumen or high-pressure air.

A portion forming the lumen 230 along the shaft 210 may be integrally molded with the shaft 210, or the lumen 230 along the shaft 210 may be formed as a lumen of a different tubular member from the shaft 210 and joined to the shaft 210 to form the lumen 230. If the portion forming the lumen 230 along the shaft 210 is integrally molded with the shaft 210, the lumen 230 can be easily formed by the extrusion molding similarly as the portion along the balloon 220. If the portion forming the lumen 230 along the shaft 210 is formed by a different tubular member from the shaft 210, it can be manufactured relatively easily no matter what the shape of the portion of the lumen 230 along the shaft 210 is. As for the materials constituting the tubular member, the materials constituting the shaft 210 described above can be referred to, and the materials constituting the tubular member may be the same as or different from the materials constituting the shaft 210. The tubular member may be joined to the shaft 210 by existing method such as adhesive bonding and welding.

The dimensions of the balloon 220 are preferably 5 mm to 300 mm in length in the longitudinal direction, and 0.5 mm to 12 mm in outer diameter when the lesion is in a blood vessel; the dimensions of the balloon 220 are preferably 10 mm to 100 mm in length in the longitudinal direction, and 3 mm to 30 mm in outer diameter when the lesion is in gastrointestinal tracts, such as the duodenal papilla.

Fixation of the shaft 210 and the balloon 220 may be done, for example, by adhesive bonding, welding, and attaching a ring-shaped member to the overlapping point of the ends of the shaft 210 and the balloon 220 to swage them. Of these, the shaft 210 and the balloon 220 are preferably fixed by welding. The welding of the shaft 210 and the balloon 220 prevents the shaft 210 and the balloon 220 from becoming detached even when the balloon 220 is repeatedly inflated and deflated, easily increasing the strength of the fixation between the shaft 210 and the balloon 220.

To introduce fluid into the shaft 210, the balloon catheter 200 may have a hub 204 at a proximal side of the shaft 210. The hub 204 preferably has a fluid inlet 206 that is connected to the flow channel of the fluid supplied to the interior of the balloon 220, and a guidewire insertion portion 205 that is connected to the guidewire insertion channel. The balloon catheter 200 having the hub 204 provided with the fluid inlet 206 and the guidewire insertion portion 205 can facilitate the operation of supplying fluid inside the balloon 220 to inflate and deflate the balloon 220 and delivering the balloon catheter 200 to a lesion site along a guidewire.

Fixation of the shaft 210 and the hub 204 may be, for example, adhesive bonding and welding. Of these, the shaft 210 and the hub 204 are preferably fixed by adhesive bonding. The adhesive bonding of the shaft 210 and the hub 204 can increase the fixing strength of the shaft 210 and the hub 204 to increase the durability of the balloon catheter 200 in the case where the material constituting the shaft 210 and the material constituting the hub 204 are different, for example, in which the shaft 210 is made of flexible material and the hub 204 is made of rigid material.

While not shown in the figures, the shaft 210 may be provided with a drug solution inlet at its proximal part. Drug solution injected through the drug solution inlet is introduced into the lumen 230 by a tube that is connected to the lumen 230, and can be released through the distal end 230d of the lumen 230 and/or the longitudinal opening 230a formed in the lumen 230 to be administered to the lesion. Unlike the case where the balloon 220 is coated with drug solution from the beginning, the drug solution can be injected and delivered to the lesion by the lumen 230 after the balloon 220 has been delivered to the lesion, which prevents the drug in the drug solution from being lost during delivery of the balloon 220 so that the drug can be effectively administered to the lesion.

The drugs contained in the drug solution injected through the drug solution inlet are not limited as long as they are pharmacologically active substances, and include, for example, non-genetic therapeutic agents, genetic agents, small molecules, cells, and other agents acceptable for pharmaceutical use. In particular, when the balloon catheter 200 is used to inhibit restenosis of the vessel after treatment in angioplasty, anti-stenosis agents such as anti-proliferative agents and immunosuppressive agents can be preferably used, which is exemplified by paclitaxel, sirolimus (rapamycin), everolimus, and zotarolimus. Only one, or two or more of these agents may be used.

The first balloon catheter 100 and the second balloon catheter 200 according to embodiments of the present invention can be appropriately combined to form a third balloon catheter. The third balloon catheter may be a balloon catheter having both the first engagement part 131 and the engagement part 231, or may be a balloon catheter having the first engagement part 131 and preferable features of the second balloon catheter 200. Such balloon catheters can prevent or reduce axial rotation of the elongate body and circumferential shift on the balloon of the elongate body, making it possible for the elongate body to become in contact with a lesion at a desired angle.

The present application claims priority based on Japanese Patent Application No. 2019-230874 filed on Dec. 20, 2019, and Japanese Patent Application No. 2019-230875 filed on Dec. 20, 2019. All the contents described in Japanese Patent Application No. 2019-230874 filed on Dec. 20, 2019, and Japanese Patent Application No. 2019-230875 filed on Dec. 20, 2019, are incorporated herein by reference.

DESCRIPTION OF REFERENCE SIGNS

100: first balloon catheter
104: hub of the first balloon catheter
105: guidewire insertion portion of the first balloon catheter
106: fluid inlet of the first balloon catheter
110: shaft of the first balloon catheter
111: outer tube of the shaft of the first balloon catheter
112: inner tube of the shaft of the first balloon catheter
120: balloon of the first balloon catheter
120e: inflating part of the first balloon catheter
120f: fixed part of the first balloon catheter
121: proximal tapered part of the first balloon catheter
122: straight tube part of the first balloon catheter
123: distal tapered part of the first balloon catheter
130: elongate body lumen
130d: distal end of the elongate body lumen
131: first engagement part
180: elongate body of the first balloon catheter
181: body tissue contacting part of the first balloon catheter
200: second balloon catheter
204: hub of the second balloon catheter
205: guidewire insertion portion of the second balloon catheter
206: fluid inlet of the second balloon catheter
210: shaft of the second balloon catheter
211: outer tube of the shaft of the second balloon catheter
212: inner tube of the shaft of the second balloon catheter
220: balloon of the second balloon catheter
220e: inflating part of the second balloon catheter
221: proximal fixed part of the second balloon catheter
222: proximal tapered part of the second balloon catheter
223: straight tube part of the second balloon catheter
224: distal tapered part of the second balloon catheter
225: distal fixed part of the second balloon catheter
230: lumen
230a: longitudinal opening
230d: distal end of the lumen
231: engagement part
233: stopper
234: insertion opening
280: elongate body of the second balloon catheter
281: body tissue contacting part of the second balloon catheter
282: incisions
C: virtual circle
D: distance from the first engagement part to the distal end of the elongate body lumen
d: major diameter of the elongate body
θ: axial rotation angle at the first engagement part and the engagement part
Ld: depth of the lumen
W(La): width of the longitudinal opening at the engagement part
W(Ld/2): width at ½ the depth of the lumen

The invention claimed is:

1. A balloon catheter, comprising:
a shaft extending in a longitudinal direction from a distal side to a proximal side;
a balloon disposed on the distal side of the shaft;
an elongate body extending along the shaft in the longitudinal direction and having a body tissue contacting part at its distal end part; and
an elongate body lumen through which the elongate body can be passed, wherein
the elongate body and the elongate body lumen are configured so that the elongate body is engaged with an inner wall of the elongate body lumen to form a first engagement part and an axial rotation angle of the elongate body is 0° to 60° at the first engagement part,
the first engagement part is located at a distal portion of the elongate body lumen between a distal end of the elongate body lumen and a position 30 cm from the distal end of the elongate body lumen toward the proximal side, the elongate body lumen is configured so that the elongate body is 360° rotatable around a rotation axial of the elongate body at a proximal end of the elongate body lumen, and a cross-sectional shape of the elongate body lumen in a direction perpendicular to the longitudinal direction varies continuously along the longitudinal direction such that the axial rotation angle of the elongate body gradually decreases as it is approaching the first engagement part from the proximal end of the elongate body lumen.

2. The balloon catheter according to claim 1, wherein the elongate body is axially rotatable by 5° to 60° at the first engagement part.

3. The balloon catheter according to claim 1, wherein the elongate body has a part having a non-circular shape in cross-section perpendicular to the longitudinal direction between the distal end of the elongate body lumen and the first engagement part, and the elongate body lumen has a part having a circular shape in cross-section perpendicular to the longitudinal direction at a side proximal to the first engagement part.

4. The balloon catheter according to claim 1, wherein the elongate body lumen extends along the shaft so as to be placed at the same position in a radial direction of the shaft.

5. The balloon catheter according to claim 1, wherein the shaft has an inner surface facing inwardly and an outer surface facing outwardly in a radial direction of the shaft, and the elongate body lumen is formed between the inner surface and the outer surface.

6. The balloon catheter according to claim 1, wherein the elongate body lumen is formed as a lumen of a tubular member, and the tubular member and the shaft are joined to each other.

7. The balloon catheter according to claim 1, wherein the first engagement part is placed at the distal end of the elongate body lumen.

8. The balloon catheter according to claim 1, wherein the balloon has an inflating part, and the balloon is fixed to the shaft so that the inflating part is not fixed to the shaft, and the distal end of the elongate body lumen is placed at a position proximal to the inflating part.

9. The balloon catheter according to claim 1, wherein the balloon has an inflating part comprising a straight tube part, a proximal tapered part placed proximal to the straight tube part, and a distal tapered part placed distal to the straight tube part, and the balloon is fixed to the shaft so that the inflating part is not fixed to the shaft, and the distal end of the elongate body lumen is placed at the proximal tapered part.

10. The balloon catheter according to claim 1, wherein the balloon has an inflating part comprising a straight tube part, a proximal tapered part placed proximal to the straight tube part, and a distal tapered part placed distal to the straight tube part, and the balloon is fixed to the shaft so that the inflating part is not fixed to the shaft, and the distal end part of the elongate body lumen is placed at the straight tube part.

11. A balloon catheter, comprising:

a shaft extending in a longitudinal direction from a distal side to a proximal side;

a balloon having an inflating part and disposed on the distal side of the shaft;

an elongate body extending along the shaft and the balloon in the longitudinal direction; and a lumen, through which the elongate body can be passed, extending along the shaft and the balloon in the longitudinal direction and having a longitudinal opening extending in the longitudinal direction, wherein the lumen has a proximal end that is provided with an insertion opening for inserting the elongate body and that is located at a proximal part of the shaft, the balloon is fixed to the shaft so that the inflating part of the balloon is not fixed to the shaft, the longitudinal opening of the lumen is disposed along an outer surface of the inflating part, and a proximal end of the longitudinal opening is located between a proximal end and a distal end of the inflating part;

the lumen has no opening between the proximal end of the lumen and the proximal end of the longitudinal opening, the elongate body and the lumen are configured so that the elongate body is engaged with a part of the longitudinal opening to prevent the elongate body from rotating by 60° or more in a rotational direction around an axis of the longitudinal direction, a width of the longitudinal opening at the engagement part is smaller than a width of the lumen at ½ a depth of the lumen, the lumen is configured so that the elongate body is 360° rotatable around the axis of the longitudinal direction at the proximal end of the lumen, and a cross-sectional shape of the lumen in a direction perpendicular to the longitudinal direction varies continuously along the longitudinal direction such that the axial rotation angle of the elongate body gradually decreases as it is approaching the engagement part from the proximal end of the lumen.

12. The balloon catheter according to claim 11, wherein the elongate body is axially rotatable by 5° to 60° at the engagement part.

13. The balloon catheter according to claim 11, wherein the elongate body is disposed in the lumen so that the elongate body is slidably movable in the lumen.

14. The balloon catheter according to claim 11, wherein a portion forming the lumen along the balloon is integrally molded with the balloon.

15. The balloon catheter according to claim 11, wherein the inflating part has a straight tube part, a proximal tapered part placed proximal to the straight tube part, and a distal tapered part placed distal to the straight tube part; and the proximal end of the longitudinal opening is placed at the proximal tapered part.

16. The balloon catheter according to claim 11, wherein the inflating part has a straight tube part, a proximal tapered part placed proximal to the straight tube part, and a distal tapered part placed distal to the straight tube part; and the proximal end of the longitudinal opening is placed at the straight tube part.

17. The balloon catheter according to claim 11, wherein the elongate body has a body tissue contacting part, and the lumen and the elongate body are configured so that the lumen and a part of the elongate body other than the body tissue contacting part are engaged with each other at the engagement part.

18. The balloon catheter according to claim 11, wherein at a side distal to a distal end of the longitudinal opening, the lumen has a stopper at the same position as a distal end of the elongate body or distal to the distal end of the elongate body.

* * * * *